United States Patent
Wand et al.

[11] Patent Number: 5,380,460
[45] Date of Patent: Jan. 10, 1995

[54] FERROELECTRIC LIQUID CRYSTAL COMPOUNDS CONTAINING CHIRAL HALOALKOXY TAIL UNITS AND COMPOSITIONS CONTAINING THEM

[75] Inventors: Michael D. Wand, Boulder; William N. Thurmes, Longmont; David M. Walba, Boulder, all of Colo.

[73] Assignee: Displaytech, Inc., Boulder, Colo.

[21] Appl. No.: 763,134

[22] Filed: Sep. 20, 1991

[51] Int. Cl.$^6$ .............. C09K 19/06; C09K 19/34; C07D 239/02; C07C 41/00
[52] U.S. Cl. .............. 252/299.6; 252/299.61; 252/299.66; 252/299.67; 568/647; 568/631; 546/339; 546/340; 544/298; 544/335; 544/224; 548/136
[58] Field of Search ............ 252/299.61, 299.66, 252/299.67, 299.01, 299.65, 299.64; 544/298, 335, 224; 546/339, 340, 186; 548/136; 568/647, 631

[56] References Cited

U.S. PATENT DOCUMENTS

| | | | |
|---|---|---|---|
| 4,911,861 | 3/1990 | Higuchi et al. | 252/299.65 |
| 4,954,600 | 9/1990 | Hachiya | 528/89 |
| 5,064,569 | 11/1991 | Geehaas et al. | 252/299.65 |
| 5,100,579 | 3/1992 | Higuchi et al. | 252/299.65 |

FOREIGN PATENT DOCUMENTS

| | | |
|---|---|---|
| 0278665 | 8/1988 | European Pat. Off. . |
| 62-111939 | 5/1987 | Japan . |
| 8705018 | 8/1987 | WIPO . |

Primary Examiner—Robert L. Stoll
Assistant Examiner—C. Harris
Attorney, Agent, or Firm—Greenlee and Winner

[57] ABSTRACT

Chiral, nonracemic compounds of the general formula:

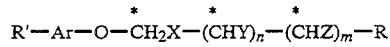

wherein m and n are either both zero, both equal one or n is equal to one and m is equal to zero, X and Y and Z are halogens, R' is an alkyl, alkoxyl, alkenyl, thioalkyl, thioether, ether, or alkylsilyl group containing three to fifteen carbon atoms, and R is an alkyl group having one to fifteen carbon atoms and where Ar is:

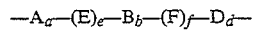

where A, B and D independently of one another are aromatic rings which are selected from the group consisting of a phenyl, a pyridine ring, a pyrimidine ring, a pyridizine ring, a pyrazine ring and a thiadiazole ring, wherein a, b and d are integers from 0–3 such that $a+b+d=2-3$, where E and F independently of one another are linking groups selected from the group consisting of a $—CH_2—CH_2—$, $—CH_2—O—$, $—CH_2—S—$, $—O—CH_2—$, $—S—CH_2$, $—OOC—$ or $—COO—$ wherein e and f can be 1 or 0, when e and/or f is 0, the adjacent aromatic rings are linked by a carbon-carbon single bond, preferably e and f are both 0 or one of e or f is 1, and wherein * indicates a chiral center, which are useful as ferroelectric liquid crystal components having high polarization are described.

29 Claims, No Drawings

FERROELECTRIC LIQUID CRYSTAL COMPOUNDS CONTAINING CHIRAL HALOALKOXY TAIL UNITS AND COMPOSITIONS CONTAINING THEM

This invention was made with partial support of the United States Government under Small Business Innovation Research grant numbers F19628-85—C-0087 and F33615-87—C5293 from the U.S. Air Force. The United States Government has certain rights in this invention.

CROSS-REFERENCE TO RELATED APPLICATIONS

This application is a division and continuation-in-part of U.S. Pat. No. 5,051,506 issued Sep. 24, 1991, which is incorporated by reference herein.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. Liquid crystal displays have a number of unique useful characteristics, including low voltage and low power of operation. In such displays, a thin layer of liquid crystal material is placed between glass plates and the optical properties of small domains in the layer is controlled by the application of electric fields with high spatial resolution. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. However, since the coupling to an applied electric field by this mechanism is rather weak, the electro-optical response time of liquid crystal based displays may be too slow for many potential applications such as in flat-panel displays for use in video terminals, oscilloscopes, radar and television screens. Fast optical response times become increasingly important for applications to larger area display devices. Insufficient nonlinearity of liquid crystal based displays can also impose limitations for many potential applications.

Electro-optic effects with sub-microsecond switching speeds can be achieved using the technology of ferroelectric liquid crystals (FLCs) of N. A. Clark and S. T. Lagerwall (1980) Appl. Phys. Lett. 36:899 and U.S. Pat. No. 20 4,367,924. These investigators have reported display structures prepared using FLC materials having not only high speed response (about 1,000 times faster than currently used twisted nematic devices), but which also exhibit bistable, threshold sensitive switching. Such properties make FLC based devices excellent candidates for light modulation devices including matrix addressed light valves containing a large number of elements for passive displays of graphic and pictorial information, optical processing applications, as well as for high information content dichroic displays.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Meyer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the chiral molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal materials which exhibit ferroelectric phases (chiral smectic C*) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing chiral smectic C* phases with useful temperature ranges can also be obtained by admixture of chiral, nonracemic compounds, designated ferroelectric liquid crystal dopants, into a liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains an (S)-2-methylbutyloxy chiral tail. Pure DOBAMBC exhibits a smectic C* phase with a ferroelectric polarization of $-3$ nC/cm$^2$.

The structures and polarization of several known smectic C* materials, including several containing phenylbenzoate cores, have been summarized in Walba et al. (1986a) J. Amer. Chem. Soc. 108:5210–5221, which also discusses a number of empirical correlations between molecular structure and FLC properties. For example, this reference (and U.S. Pat. No. 4,556,727) reports FLC compounds which contain nonracemic 2-alkoxy-1-propoxy tail units, derived from lactic acid, coupled to 4-substituted phenylbenzoate cores:

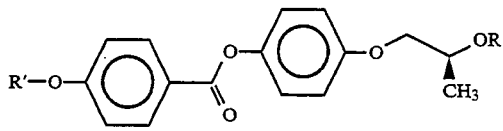

where R is a lower alkyl group containing one to three carbon atoms and R' is an alkyl group containing nine to twelve carbon atoms. These compounds possess monotropic smectic C* phases which display fast switching speeds at room temperature. It is also reported therein that certain eutectic mixtures containing these FLC compounds possess thermodynamically stable or enantiotropic smectic C* phases with high polarization density and fast electro-optical switching speeds.

Walba et al. (1986) J. Amer. Chem. Soc. 108:7424–7425 and Walba and Vohra, U.S. Pat. No. 4,638,073 disclose ferroelectric smectic liquid crystal compounds possessing a high ferroelectric polarization density having chiral tail units derived from (2,3)-alkyloxiranemethanols and achiral phenylbenzoate and biphenyl core units. The ferroelectric crystal materials reported have the following general formulas:

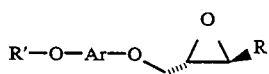

where R is an alkyl of one to seven carbon atoms and R' is an alkyl of five to twelve carbon atoms and Ar is phenylbenzoate or biphenyl.

Eidman and Walba, [U.S. Pat. No. 4,777,280] discloses chirally asymmetric liquid crystals possessing the phenylbenzoate core unit and 1-cyanoalkoxy chiral tails.

Walba and Razavi, [U.S. Pat. No. 4,695,650] discloses chirally asymmetric compounds possessing a reverse ester phenylbenzoate core unit with 1-fluoro or 1-chloroalkyl group chiral tail units having the general formula:

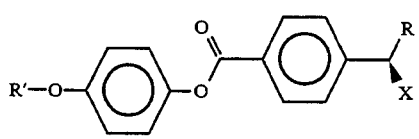

wherein R is an alkyl group of three to twelve carbon atoms, R' is an alkyl of five to twelve carbon atoms, and X is a chlorine atom or a fluorine atom. These materials impart the property of high polarization density in mixtures which display an FLC phase and are useful as FLC dopants.

Walba and Razavi, [U.S. Pat. No. 4,835,295] discloses chirally asymmetric phenyl and biphenylbenzoates having chiral 2,3-epoxy alkyl or 1-halo-2,3-epoxy alkyl tails which are useful as components of FLC materials. The compounds disclosed have the formula:

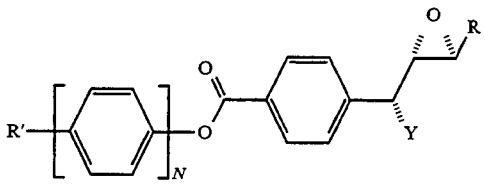

where R' is an alkyl or alkoxyl group having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and faster switching speeds in FLC mixtures than their diastereomers of formula B. It is suggested that the difference in properties of A and B is due to the

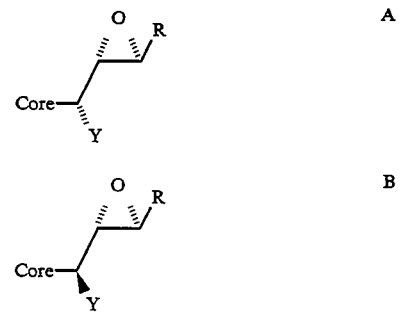

relative alignment of the epoxide and halogen bond dipoles in the isomers.

Higuchi et al. U.S. Pat. No. 4,695,651 disclose biphenyl-based diester liquid crystal compounds having the general formula:

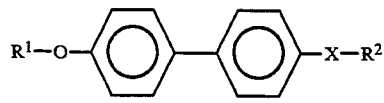

wherein $R^1$ and $R^2$ represent $C_{1-18}$ alkyl, alkyl halide or aralkyl halide groups and X is —$COOCH_2$— or —OCO—. Compounds in which the $R^2$ group contains an asymmetric carbon are disclosed, although no specific stereochemistry is specified. The liquid crystal materials disclosed are said to display ferroelectricity. In related work, Higuchi et al. U.S. Pat. No. 4,592,858 disclose chiral smectic liquid crystal compounds having biphenyl cores attached by an ester linkage to an optically active group as in the formula:

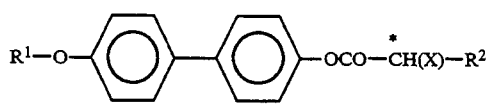

wherein the carbon marked with * is an asymmetric carbon, X is chloro or bromo and $R^2$ is a branched-alkyl group. These compounds are said to exhibit strong ferroelectricity. The stereochemistry of the optically active center is not specified.

Krause et al. in PCT application EP 8600248, publication No. WO 8606373, disclose optically active nitrogen containing heterocycles which are reported to be useful as constituents for FLC materials. Phenylpyrimidines substituted with optically active groups, including haloalkyl groups are disclosed. The stereochemistry of the optically active centers is not specified.

While several useful ferroelectric liquid crystal materials (both pure compounds and mixtures) have thus been reported, optimum response times have not been achieved (theoretical limit estimated as 10–50 nsec, Walba et al. (1986a), supra). For this reason, new FLC materials particularly those having high polarization density and low viscosity are desirable, as are new FLC dopants which can impart desired properties to FLC materials. A useful property of FLC dopants is good miscibility in smectic C* matrix materials.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds on low polarization materials when mixed with such materials to form ferroelectric liquid crystal compositions. Alternatively, certain of the compounds of the present invention in pure form can also possess stable smectic C* phases having high polarization density.

The compounds of the present invention are prepared by the incorporation of enantiomerically enriched 2-haloalkoxy, 2,3-dihaloalkoxy or 2,3,4-trihaloalkoxy tails into a suitable liquid crystal core (R'-Ar). In general, suitable cores are rigid, linear moieties. Preferred cores are those that are chemically stable and which do not impart high orientational viscosity in the liquid crystal phase. Cores of the present invention have at least one aromatic ring. Preferred rings have two or three aromatic rings. Aromatic rings of the core can be directly linked by a single bond, e.g., biphenyl, bi-pyridyl or phenylpyrimidine, or linked through a group containing one or more carbons or heteroatoms, e.g., —CH$_2$—CH$_2$—, —COO—, —OOC—, —CH$_2$—O—, —CH$_2$—S—, —O—CH$_2$— or —S—CH$_2$—. The aromatic rings of the core can be phenyl rings as well as aromatic rings containing one or two nitrogens, for example, a pyridine, a pyrimidine, a pyrazine, a pyridizine, or a thiadiazole. The aromatic rings can be arranged within the core in any order. Preferred cores contain aromatic rings linked in para, linear arrangement.

Aromatic rings of the core can include, but are not limited to:

1,4-substituted phenyl ring: 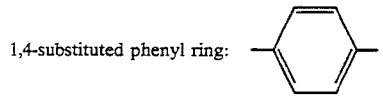

2,5-substituted pyridine ring: 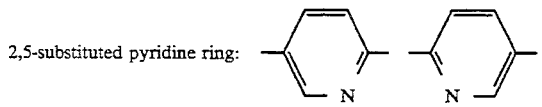

2,5-substituted pyrimidine rings: 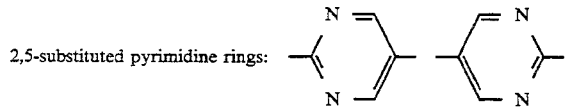

-continued 3,6-substituted pyridizine ring: 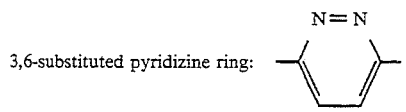

2,5-substituted pyrazine ring: 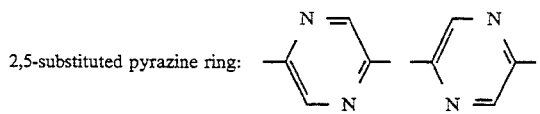

2,5-substituted thiadiazole ring: 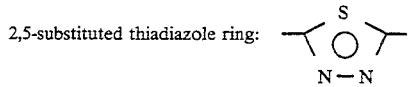

The chiral tail units and R' tail units are preferably linked on opposite ends of the core in a para arrangement. The aromatic rings of the core can be arranged within the core in any order with respect to the R' and chiral tail unit. In the present invention cores containing two or three aromatic rings are preferred such as those cores based on a phenylbenzoate, biphenylbenzoate, phenyl-substituted phenylbenzoate, phenylpyrimidine, phenylpyridine, phenylbenzoate pyrimidine, phenylbenzoate pyridine, or biphenyl structure.

Specific core units include: 4-R'-biphenyl phenylpyrimidine and 4-R'-biphenylbenzoate, 5-R',2-phenylpyridine, 2-(4-R'-phenyl) pyrimidine, 2-(4-R'-phenyl) pyridine, 2-R',5-phenylpyrimidine, 5-R',2-phenylbenzoatepyrimidine, 5-R',2-phenylbenzoate pyridine, 3-(4-R'-phenyl) pyridine 5-(4-R'-phenyl) pyrimidine, 2-R',5-phenylbenzoate pyrimidine and 2-R',5-phenylbenzoate pyridine. Exemplary Ar cores include, but are not limited to those of Table 1 in which the chiral nonracemic tail unit is R*.

The chiral nonracemic compounds of the present invention have R' which may or may not be chiral. R' tails of the present invention include alkyl, alkenyl, alkoxy, thioalkyl, thioether or silylalkyl groups having three to fifteen carbon atoms. The R' tail units may be straight chain or branched. Alkenyl R' tails preferably have a one double bond and more preferably have an e-double bond. R' tails include thioalkyl tails, e.g., R'=C$_n$H$_{2n}$—S—, and thioether tails, e.g., C$_n$H$_{2n}$—S—CH$_2$—, preferably contain one sulfur atom. R' tails also include silylalkyl tails, e.g., C$_n$H$_{2n}$—Si(CH$_3$)$_2$—CH$_2$—, or (CH$_3$)$_3$ Si—C$_n$H$_{2n}$—, where a dialkylsilyl group such as (CH$_3$)$_2$Si is inserted within an alkyl chain. R' tails of the present invention are most preferably alkyl, alkoxy and e-alkenyl tails. R' tails contain three to fifteen carbon atoms. Non-adjacent carbon atoms in the tail can be replaced with a double bond, sulfur atom, oxygen atom or dialkylsilyl group such as (CH$_3$)$_2$Si. R' tails more preferably contain five to twelve carbon atoms.

The chiral tail units of the present invention contain halogen atoms. Preferably the halogens are fluorine and chlorine. Most preferably, the halogens are fluorine. The R group of the chiral tail units may be alkyl or alkenyl and contain one to fifteen carbon atoms. More preferably, the R group of the chiral tail has from two to eight carbon atoms. Most preferably, the R group is an alkyl group having two to eight carbon atoms. These alkyl and alkenyl groups can be straight-chain or branched, straight-chain being preferred.

The 2-haloalkoxy compounds of the present invention are represented by formula III (Scheme II); the 2,3-dihaloalkoxy compounds by formulas I and II (Scheme I); and the 2,3,4-trihaloalkoxy compounds by formulas IV–VII. More specifically, attachment of these enantiomerically enriched haloalkoxyl tails to the para position of suitable core units results in compounds which are useful in the preparation of ferroelectric liquid crystal materials, either in pure form or as a component in an FLC mixture.

An important feature of the present invention is the finding that the 2,3-dihaloalkoxy compounds of formula I effect much faster switching speeds in FLC mixtures than the analogous diastereomers of formula II. This indicates that compounds of formula I have much higher extrapolated polarization densities than the diastereomers of formula II. This effect is believed to result from the relative alignment of the alkoxy oxygen and halogen bond dipoles in the preferred conformation of the diastereomers in the FLC phase. 2,3,4-trihaloalkoxides of formula IV also effect faster switching speeds in FLC materials than the analogous diastereomers of formulas V–VII, due to an analogous alignment of bond dipoles.

Another surprising finding of the present invention is that the 2,3-dihaloalkoxide regioisomers, as in I, where X is not equal to Y, have significantly different properties in FLC materials. The regioisomers in which F is positioned closer to the core, i.e., in the 2-position, effect faster switching speeds in FLC mixtures than those isomers in which F is further from the core, i.e., in the 3-position. Similarly, 2,3,4-trihaloalkoxide regioisomers of the present invention in which the X substituent is F effect faster switching speeds in FLC mixtures than those trihalide isomers in which F is further from the core.

Specifically, the present invention provides chiral nonracemic mono-, di- and trihaloalkoxides of the formula:

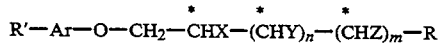

wherein:

Ar is an achiral core unit containing at least one aromatic ring, where Ar is

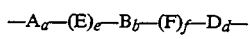

where A, B and D independently of one another are aromatic rings which are selected from the group consisting of a phenyl, a pyridine ring, a pyrimidine ring, a pyridizine ring, a pyrazine ring and a thiadiazole ring, wherein a, b and d are integers from 0–3 such that $a+b+d=2-3$, where E and F independently of one another are linking groups selected from the group consisting of a —CH$_2$—CH$_2$—, —CH$_2$—O—, —CH$_2$—S—, —O—CH$_2$—, —S—CH$_2$, —OOC— or —COO— wherein e and f can be 1 or 0. When e and/or f is 0, the adjacent aromatic rings are linked by a carbon-carbon single bond. Preferably e and f are both 0 or one of e or f is 1.

More specifically, A, B and D are independently of one another aromatic rings selected from the group of rings including 1,4-substituted phenyl, 2,5-substituted pyridine, 2,5-substituted pyrimidine, 3,6-substituted pyridizine, 2,5-substituted pyrazine and 2,5-substituted thiadiazole. Preferred cores are those including phenyl, pyridine, pyrimidine, pyridizine or pyrazine rings.

R' is an alkyl, alkoxyl, alkenyl, thioalkyl, thioether, ether, or alkylsilyl group containing three to fifteen carbon atoms, and n and m can be both equal to zero (for monohalides), n can be equal to one and m equal to zero (for dihalides) or n and m can be both equal to one (for trihalides), when n and m are both equal to zero, X is a halide and R is an alkyl group having two to fifteen carbon atoms, when n is equal to one and m is equal to zero, X is a halide, Y is a halide and R is an alkyl group having from one to fifteen carbon atoms, and when n and m are both equal to one, X, Y and Z are halides and R is an alkyl or alkenyl group having from one to fifteen carbon atoms wherein * indicates an asymetric carbon. The alkyl and alkenyl groups can be straight chain or branched.

Cores of the present invention which contain only one —CH$_2$—CH$_2$—, —COO—, —OOC—, —CH$_2$—O—, —O—CH$_2$—, —CH$_2$—S—, or —S—CH$_2$— linkage are preferred.

Cores may contain one or more phenyl rings in combination with aromatic nitrogen-containing rings. Cores may contain two or three aromatic nitrogen-containing rings, particularly those in which e and f are both zero.

Preferred two ring cores include biphenyl, 2-phenylpyridine, 5-phenylpyridine, 2-phenylpyrimidine, 5-phenylpyrimidine, 3-phenylpyridizine, 6-phenylpyridizine, 2-phenylpyrazine, 5-phenylpyrazine, phenylbenzoate, pyridinebenzoate, pyrimidinebenzoate, bipyridine, bipyrimidine, and pyridinepyrimidine.

Preferred three ring cores include phenyl-substituted phenylbenzoate, biphenylbenzoate, pyridine-substituted phenylbenzoate, pyrimidine-substituted phenylbenzoate, phenyl-substituted pyrimidinebenzoate, and phenyl-substituted pyridinebenzoate.

The preferred thiadiazole-containing core is 2,5-diphenylthiadiazole.

R' that is an alkyl group, alkenyl group, alkoxy group, ether group, thioalkyl group or thioether group is preferred. R' that is an alkyl group, e-alkenyl group or alkoxy group is more preferred.

R that is an alkyl or alkenyl group having two to eight carbons is more preferred. R that is an alkyl having two to eight carbons is more preferred.

Compounds in which Ar contains two or three aromatic rings are preferred; two ring cores being more preferred. It is preferred that X, Y and Z are fluorine or chlorine atoms. It is more preferred that X, Y and Z are fluorine atoms.

Cores of the present invention are exemplified by those listed in Table 1. The cores of the present invention include, but are not limited to, those listed in Table 1.

More specifically, in one aspect, this invention provides 2-monohaloalkoxides of the formula:

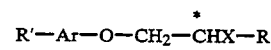

wherein Ar is —A$_a$—(E)$_e$—B$_b$—(F)$_f$—D$_d$— as defined above.

R' is an alkyl, alkenyl, alkoxy, thioalkyl, thioether, ether, or alkylsilyl group having from three to fifteen carbon atoms, as defined above.

X is a halogen,

R is an alkyl or alkenyl group having from one to fifteen carbon atoms and wherein * indicates an asymmetric carbon.

Monohaloalkoxides in which Ar is 4,4'-substituted phenylbenzoate, 5,4-substituted 2-phenylpyrimidine or 4,4'-substituted biphenyl are preferred, the phenylbenzoates and phenylpyrimidines are more preferred. R' of any type preferably contains five to twelve carbon atoms. R is preferably alkyl or alkenyl having two to eight carbon atoms. R is more preferably alkyl containing two to eight carbon atoms. It is preferred that X be a fluorine or a chlorine atom and most preferred that X be a fluorine atom.

In a second aspect, this invention specifically provides chiral nonracemic 2,3-dihaloalkoxides of the formula:

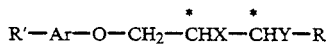

$$R'-Ar-O-CH_2-\overset{*}{C}HX-\overset{*}{C}HY-R$$

wherein:
Ar is $-A_a-(E)_e-B_b-(F)_f-D_d$, as defined above.
R' is as defined above.
X is a halogen,
Y is a halogen,
R is as defined above.

Those dihaloalkoxides in which R' contains five to twelve carbons are preferred and in which R contains two to eight carbon atoms are preferred. R which is an alkyl containing two to eight carbon atoms are more preferred. It is preferred that X and Y be fluorine or chlorine atoms. It is preferred that X, the 2-substituent, be a fluorine. It is more preferred that both x and y are fluorines.

In a particular embodiment of the present invention, 2,3-dihaloalkoxides having the structure of formula I are provided, wherein X and Y are halogens, R' is as described above. R is as defined above and the achiral core, Ar, is $-A_a-(E)_e-B_b-(F)_f-D_d$, as defined above. Compounds of formula I will have higher polarization densities than those of their diastereomer of formula II.

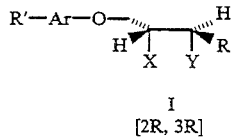

I
[2R, 3R]

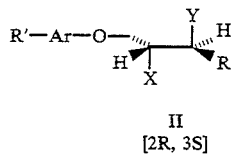

II
[2R, 3S]

In compounds of formula I, R' preferably contains five to twelve carbons and R is preferably an alkyl or alkenyl having three to eight carbon atoms and more preferably is an alkyl containing three to eight carbon atoms. It is preferred that X and Y be fluorine or chlorine atoms. It is preferred that X, the 2-substituent, be a fluorine. It is more preferred that X and Y are fluorine.

In a third aspect, this invention provides chiral nonracemic 2,3,4-trihaloalkoxides of the formula:

$$R'-Ar-O-CH_2-\overset{*}{C}HX-\overset{*}{C}HY-\overset{*}{C}HZ-R$$

wherein:
Ar is $-A_a-(E)_e-B_b-(F)_f-D_d$, as defined above.
R' is as defined above.
X, Y and Z are halogens,
R is as define above.

Tri-haloalkoxides in which R' contains five to twelve carbons are preferred. Those in which R is an alkyl or alkenyl group preferably contain two to eight carbon atoms and R which is an alkyl having two to eight carbons is more preferred. Compounds in which X, Y and Z are fluorine or chlorine are preferred. Compounds in which X is fluorine are more preferred. Compounds in which X, Y and Z are fluorine are more preferred.

In a particular embodiment, 2,3,4-trihaloalkoxides having the structure of formula IV are provided, wherein X, Y and Z are halogens, Ar is $-A_a-(E)_e-B_b-(F)_f-D_d-$ as defined above, R' is as defined above, and R is as defined above. Alkyl and alkoxy R' and R groups can be straight chain or branched. Compounds of formula IV will display higher polarization densities in FLC phases than the corresponding diastereomers (V-VII).

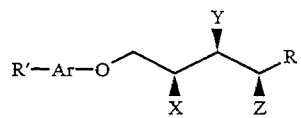

IV, [2S, 3S, 4R]

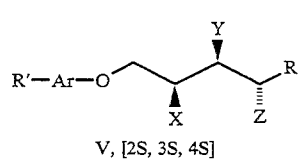

V, [2S, 3S, 4S]

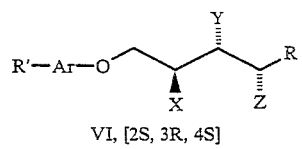

VI, [2S, 3R, 4S]

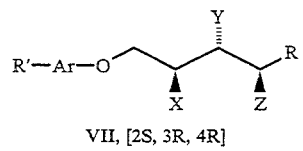

VII, [2S, 3R, 4R]

Compounds of formula IV in which R' contains five to twelve carbons are preferred and in which R is an alkyl or alkenyl group containing two to eight carbon atoms are preferred. Those in which R is an alkyl group and contain two to eight carbon atoms are more preferred. It is preferred that X, Y and Z be fluorine or chlorine atoms. It is preferred that X be a fluorine atom. Compounds in which X, Y and Z are fluorine are more preferred.

TABLE 1
EXAMPLES OF TWO AND THREE RING CORES
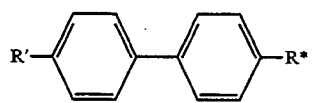 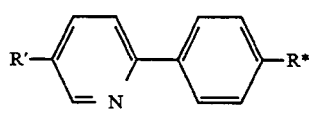
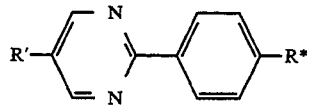 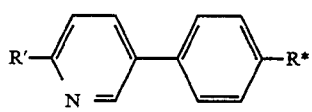
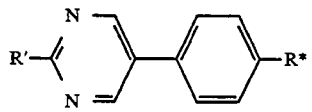 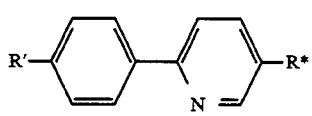
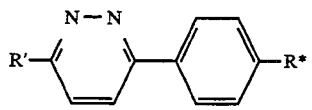 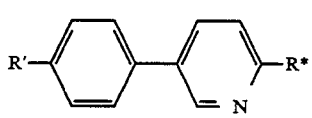
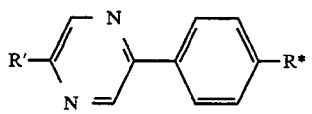 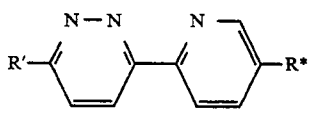
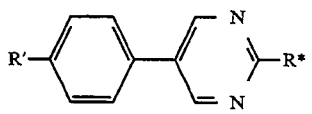 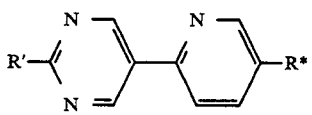
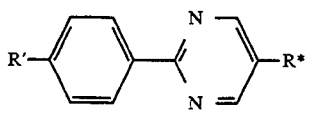 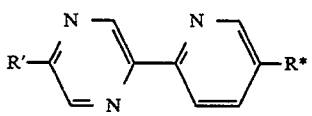
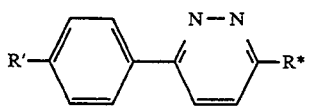 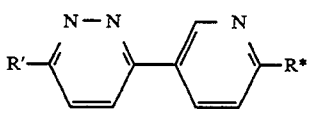
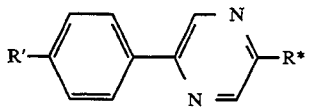 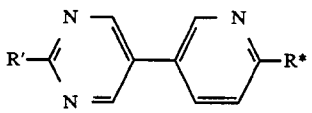
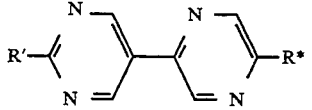 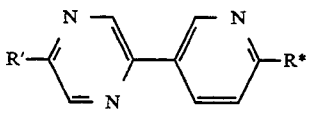
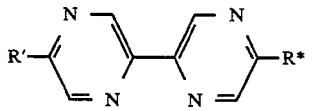 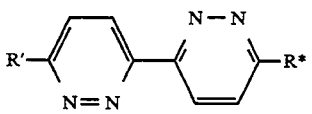
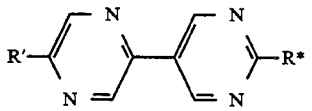 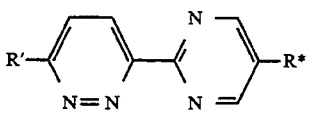
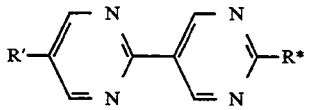 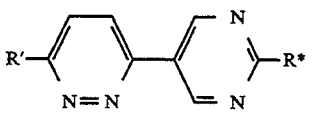

TABLE 1-continued
EXAMPLES OF TWO AND THREE RING CORES
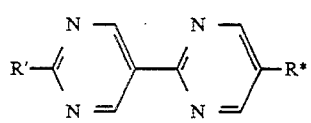 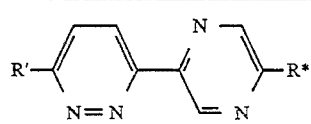
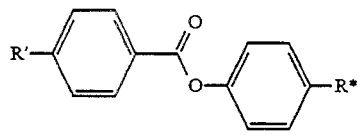 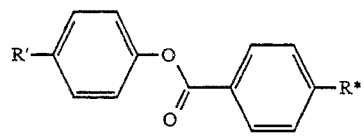
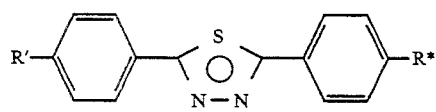 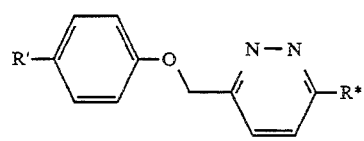
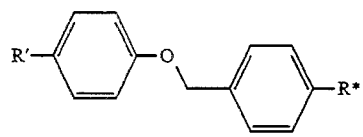 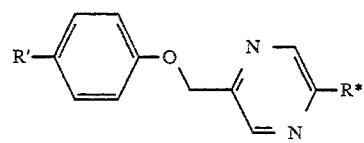
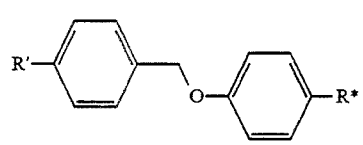 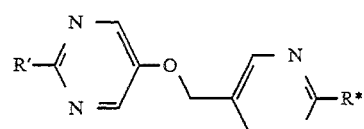
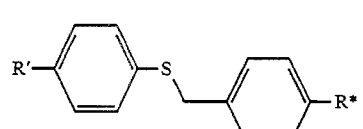 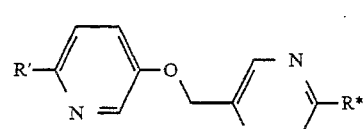
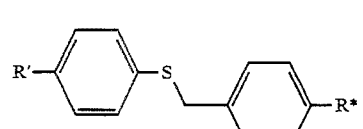 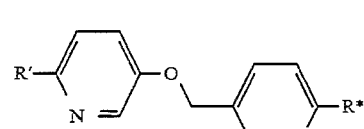
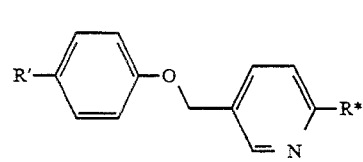 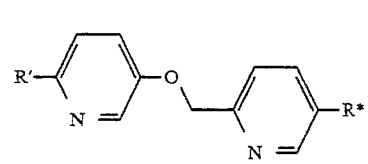
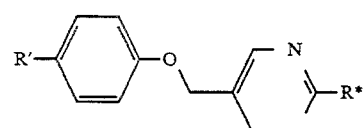 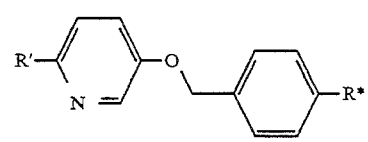
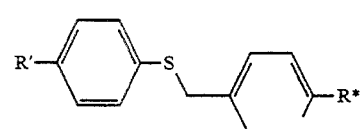 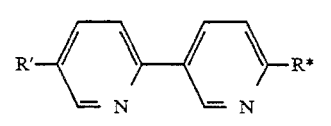

TABLE 1-continued
EXAMPLES OF TWO AND THREE RING CORES
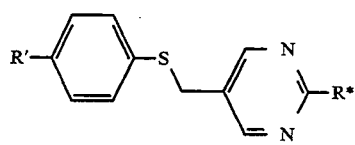 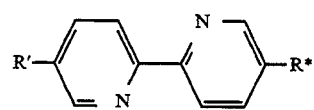
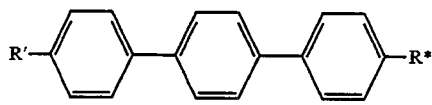 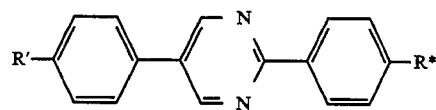
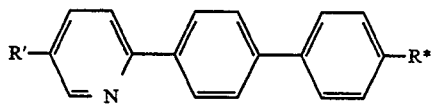 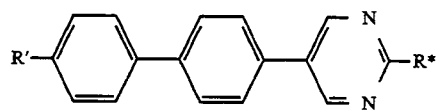
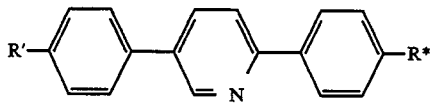 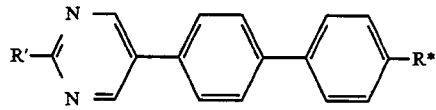
 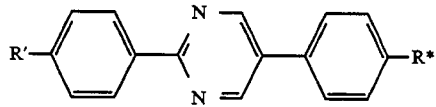
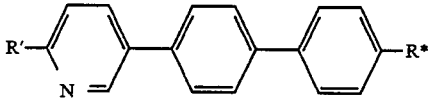 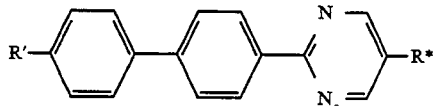
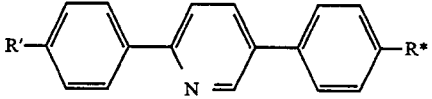 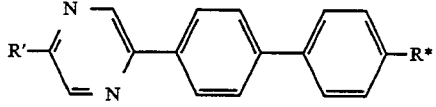
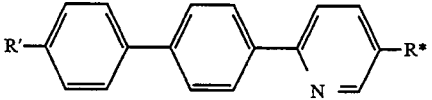 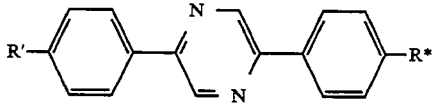
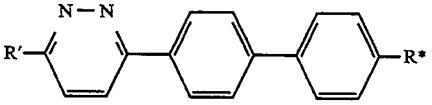 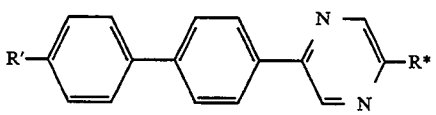
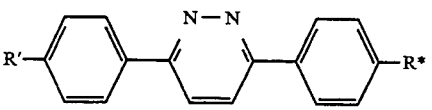 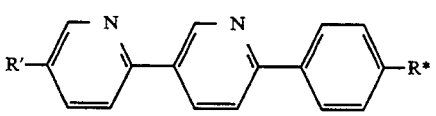
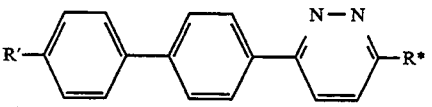 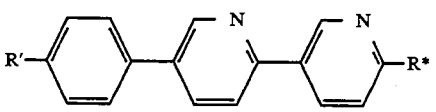
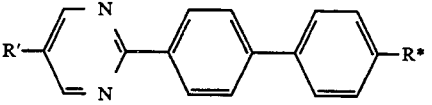 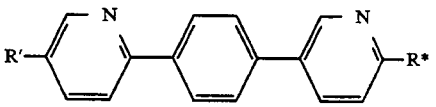

5,380,460
TABLE 1-continued
EXAMPLES OF TWO AND THREE RING CORES
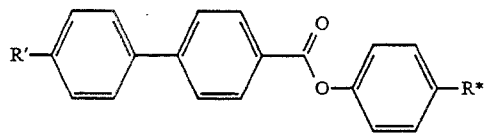
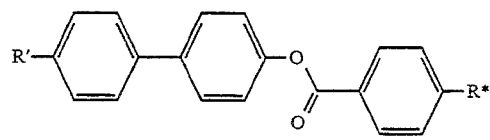
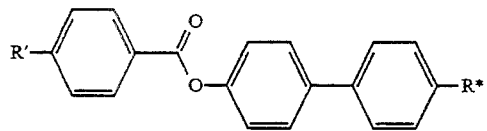
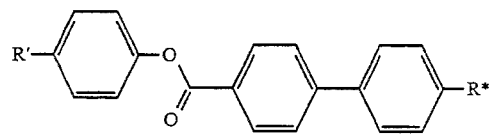
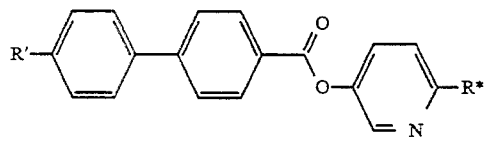
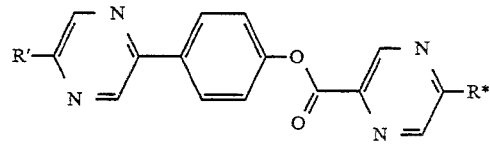
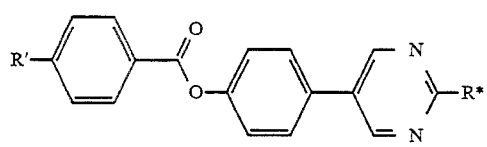
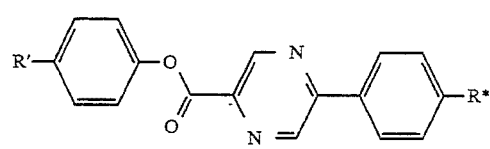
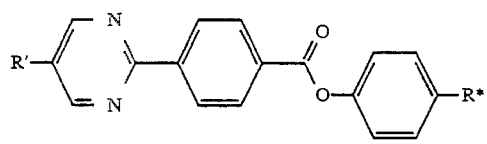
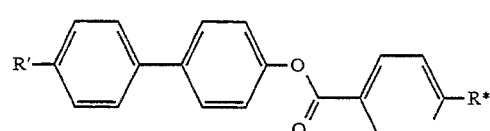
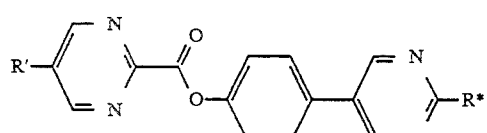
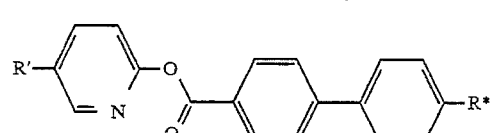
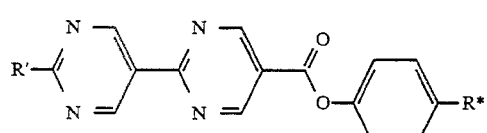
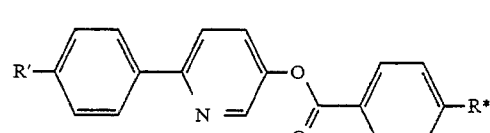
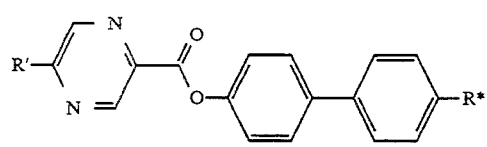
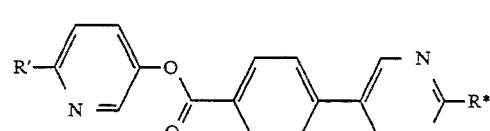
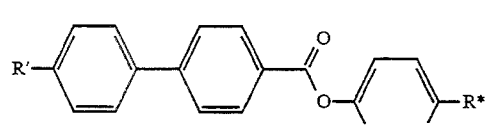
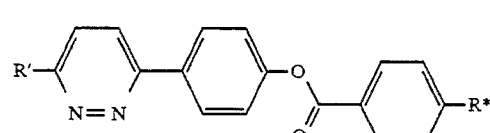
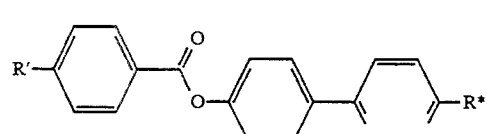
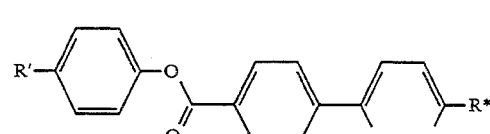

TABLE 1-continued
EXAMPLES OF TWO AND THREE RING CORES

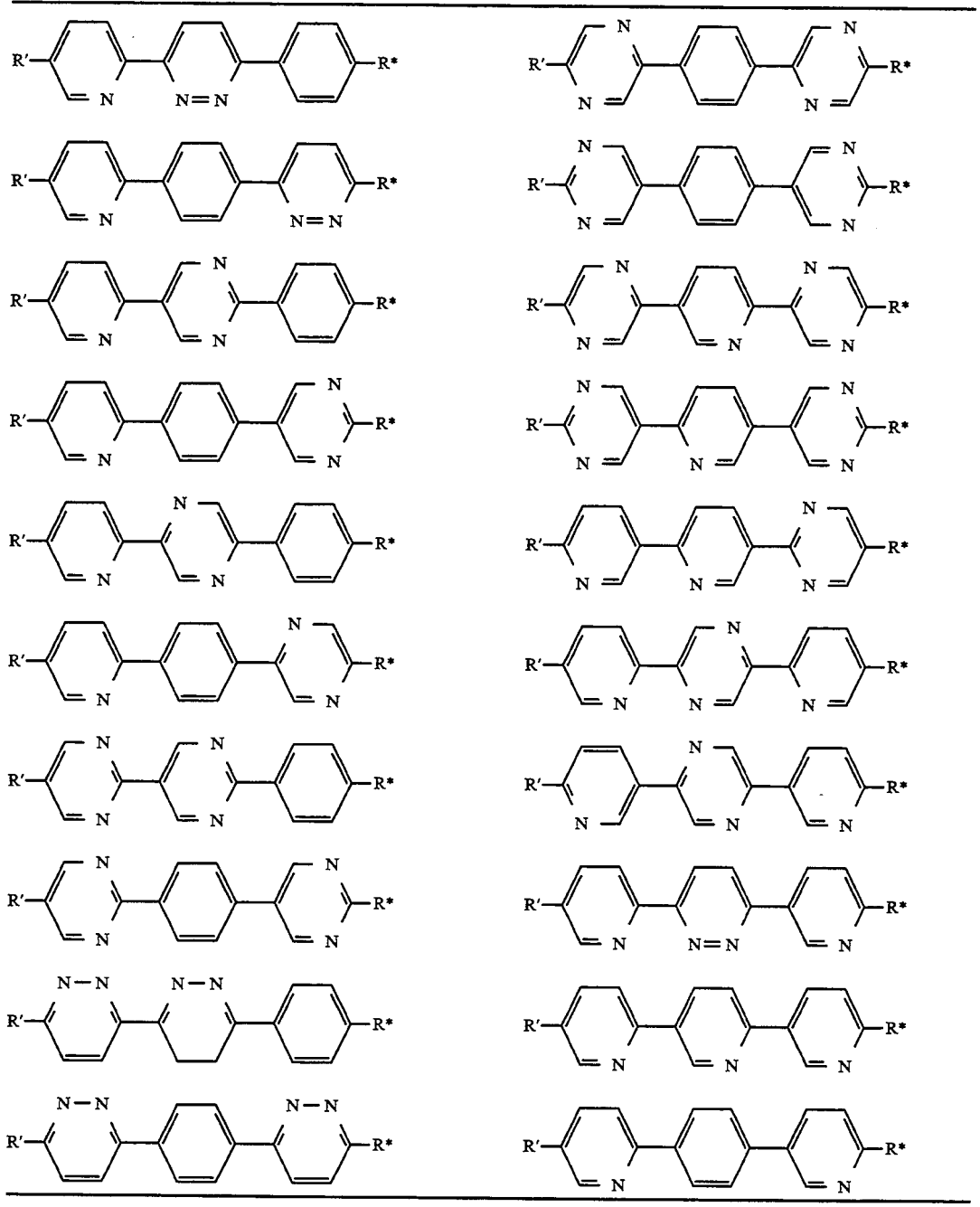

DETAILED DESCRIPTION OF THE INVENTION

The ferroelectric liquid crystal compounds of formulas I and II are prepared from chiral 2,3 epoxides according to the general reaction Scheme I. In general terms compounds of formula I are prepared from the chiral nonracemic transepoxides of formula VIII. Initial acid catalyzed epoxide ring opening to give the halohydrin isomers of formulas IX A and B, is followed by stereospecific halogen substitution, which proceeds with inversion at the site of substitution, to give the dihalide of formula I. When X is not the same halogen as Y, two chiral nonracemic regioisomers, I (A and B) are produced. Dihalides of formula II are prepared by analogous methods starting with a chiral, nonracemic cis-epoxide of formula X.

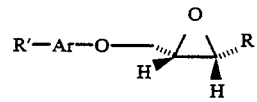

If the halogen substitution reaction of Scheme I, is only stereoselective, i.e., if a mixture of retention and inversion occurs, then a mixture of diastereomeric dihalides of formulas I and II will result (see Scheme I). In such a case, the resultant mixture of diasteromers can be separated by application of conventional chromatographic techniques.

Compounds of formulas I and II each represent one of a pair of enantiomers. The pair of enantiomers of each compound will function in a complementary manner. For illustration, the structures of the enantiomers of the difluoride (I and I', where X=Y=F) are shown:

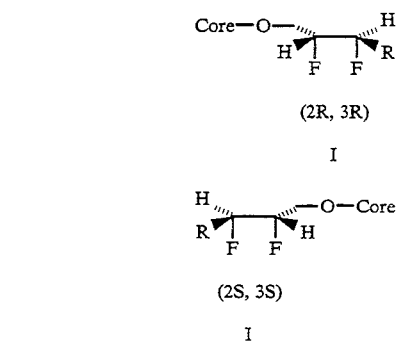

Scheme I

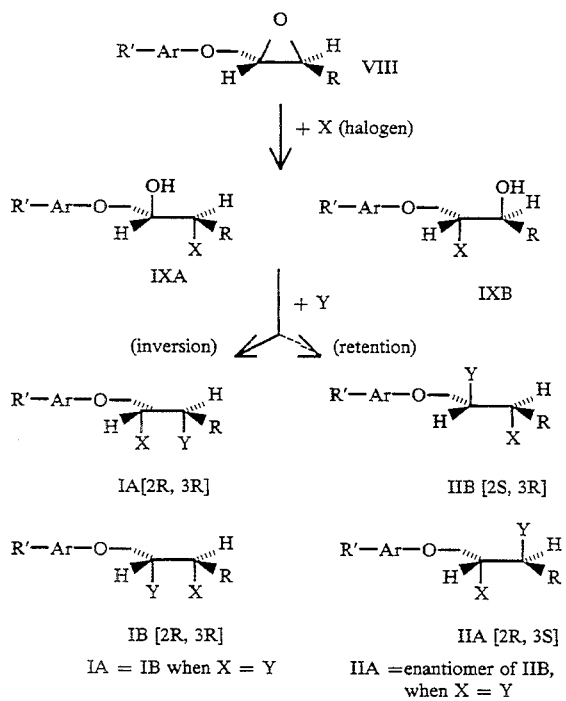

IA = IB when X = Y   IIA = enantiomer of IIB, when X = Y

Compound I will function equivalently to its enantiomer of formula I' in FLC materials, except that the sign of E will be reversed. As will be understood by those in the art, the sign of the polarization of an FLC dopant should be the same as that of the host material in order to achieve high polarization mixtures. It is a feature of this invention that either enantiomer of the compounds of formulas I or II can be prepared. This allows choice of the appropriate enantiomer for use with a particular host material. The enantiomers of compounds of formulas I and II can be prepared from the appropriate enantiomer of formula VIII or X, respectively, by the methods described herein.

The chiral epoxides of formulas, VIII or X, can be prepared by known methods by coupling of the appropriate chiral epoxy bromides (or in some cases epoxy alcohols) with substituted phenols (XI):

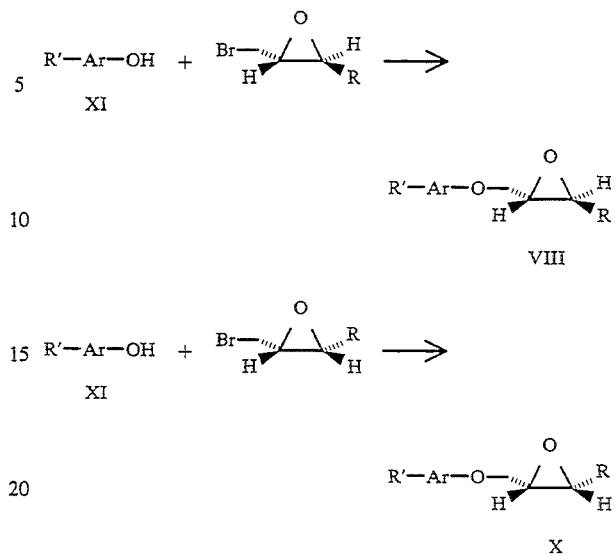

The chiral epoxy bromide (or alcohol) and the substituted phenol starting materials are in turn produced by known methods from readily available starting materials.

The ferroelectric liquid crystal compounds of the present invention having chiral 2-haloalkoxy tails, formula III, can be prepared as exemplified in Scheme II. The synthesis proceeds through a chiral 2-halo alcohol. This halo alcohol intermediate is coupled to a desired core unit by known means as, for example, described herein in the examples. The chiral 2-halo alcohol is made starting with a chiral nonracemic α-hydroxyester (XII), such as D-methyl α-hydroxyisocaproate (where R=iso-propyl). Stereospecific halogenation of the alcohol, for example employing KF or CsCl/18-crown-6 in acetonitrile results in the desired chiral monohalo alcohol intermediate (XIII).

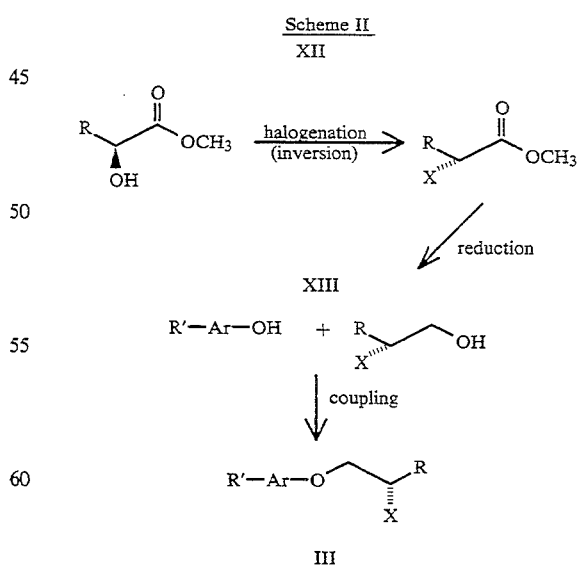

The monohalides of formula III contain a single asymmetric center having two enantiomeric forms, III and III'. As noted above both enantiomers will function in an equivalent manner in ferroelectric crystal materials, except that the sign of the polarization of the enantiomers will be reversed.

The ferroelectric liquid crystal compounds of the present invention having chiral 2,3,4 trihaloalkoxy tail units can be prepared as exemplified in Scheme III, for preparation of a trihalide of formula IV. In general, a regioselective Schlosser-Wittig trans olefination (Schlosser, M. et al. (1970) Chem. Ber. 103:2314) is performed on the chiral acetonide of glyceraldehyde, in this case on (R)-glyceraldehyde acetonide and the resulting product is deprotected with acid to give the substituted chiral trans olefin-1,2(R) diol (XIV). The alkyl substitutent of the diol is selected by use of an appropriately substituted Wittig reagent. Selective protection of the primary alcohol with a hindered reagent, P-Cl in Scheme III, such as trimethylacetyl chloride, followed by stereospecific epoxidation of the olefin, using for example a Sharpless epoxidation with S(+) diethyltartrate (Martin et al. (1981) J. Amer. Chem. Soc. 103:2637), to give an excess of the syn-hydroxyepoxide which is then treated with an SN2-type halogenation agent to result in the chiral haloepoxy protected alcohol (XV). The halo epoxide intermediate is then steroselectively halogenated, as has been described for the epoxides (VIII) in Scheme I, and deprotected to obtain a chiral trihalo alcohol. The trihalo alcohol, which has the 2S,3S,4R stereochemistry results from inversion of configuration with each halogenation (triple inversion). Any retention of configuration, for example on halogenation of the epoxide, results in the production of diastereomers of the 2S,3S,4R trihalo alcohol, as shown in Scheme III. Mixtures of diastereomeric products can be separated using conventional chromatographic techniques. The chiral trihalo alcohols are then coupled to an achiral core unit, R'—Ar—OH, such as the 5-R'-substituted pyrimidine phenol, to give the desired chiral, nonracemic ferroelectric liquid crystal material IV. Coupling to core units is achieved as described in the Examples.

The enantiomer of the 2S,3S,4R trihalo alcohol intermediate, the 2R,3R,4S trihalo alcohol, is prepared by the method of Scheme III, employing the (S)-glyceraldehyde acetonide. Replacing the Schlosser-Wittig reaction step in Scheme III with a conventional Wittig reaction results in a cis-olefin intermediate. Starting with the R-glyceraldehyde acetonide, proceeding through the cis-olefin intermediate, followed by stereospecific epoxidation and stereospecific halogenation with inversion results in 2S,3S,4S trihalo alcohol, which on coupling to the core give the compound of formula V. It will be readily apparent to those in the art that each of the compounds IV–VII can be prepared by variation of the stereochemistry of the starting material, choice of regioisomer intermediate and variation in the stereoselectivity of the halogenation reactions in the method described above.

An alternative method can be employed, as shown in Scheme IV, to prepare the chiral trihalo alcohol intermediates and subsequently the ferroelectric liquid crystal materials IV where X, Y and Z are the same halogen. In this method, a nonracemic sugar is converted by a series of reactions to a chiral nonracemic aldehyde bearing protective groups, such as acetate groups (OAc), at the 2,3 and 4 positions. The protective groups are then replaced with halogens by stereospecific or stereoselective halogenation to give a chiral, nonracemic trihaloaldehyde,

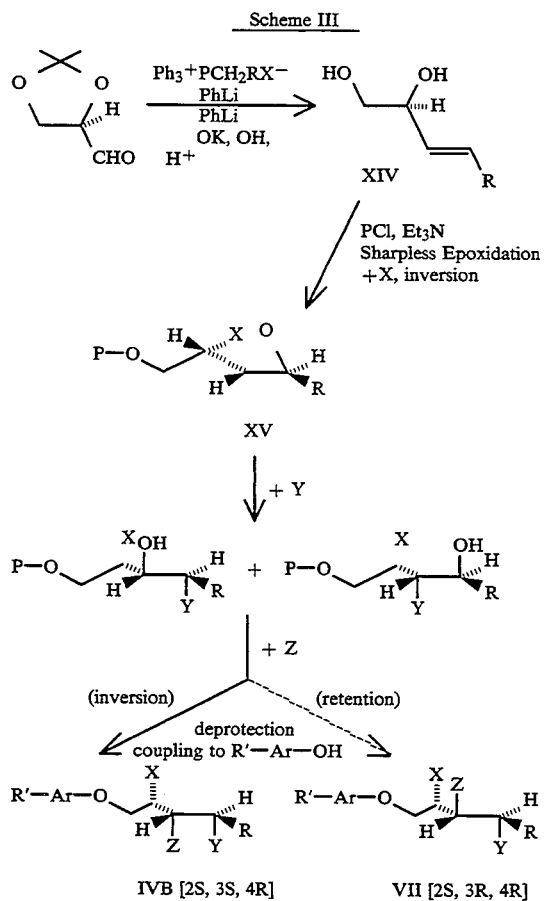

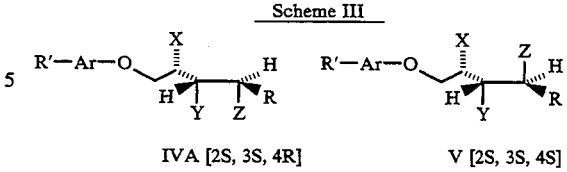

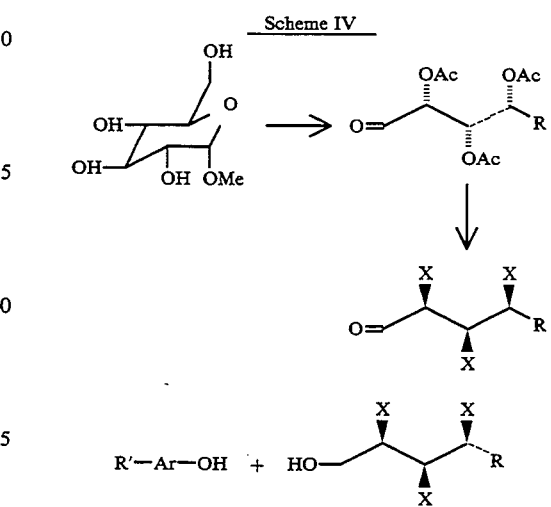

-continued
Scheme IV

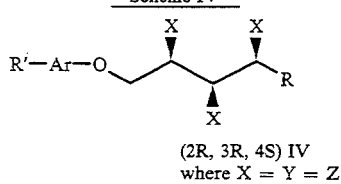

(2R, 3R, 4S) IV
where X = Y = Z which can be reduced to give a chiral, nonracemic 2,3,4 trihalo alcohol.

The trihalo alcohol intermediate is then coupled to a desired achiral core unit, for example a phenylpyrimidine, phenylbenzoate, biphenyl or related core, by known methods to produce the compounds of formula IV. For example by coupling of the alcohol intermediate to a 2-phenylpyrimidine core employing DEAD (diethylazodicarboxylate) and triphenylphosphine. Methods analogous to those described in the Examples can be employed to synthesize the analogous compounds having Ar cores.

In the method of Scheme IV, the stereochemistry of the trihaloalcohol intermediate is selected by choice of the chiral sugar starting material. Appropriate sugar starting materials are available from commercial sources or can be prepared by conventional methods from known starting materials. For example, the conversion of the α-methyl pyranoside of D-galactose via the reactions of Scheme IV, results in a 2R,3R,4R-trifluoro alcohol and subsequently in the 2R,3R,4R-trifluoroalkoxide which is the enantiomer of compounds of formula V. Similarly, conversion of the α-methyl pyranoside of mannose results in the 2S,3R,4S-trifluoro alcohol intermediate and ultimately in the corresponding compound of formula VI.

Due to the presence of three stereocenters, the trihaloalkoxy compounds of the present invention can have any of four diastereomeric structures: IV-VII. Each of the diastereomers represents two enantiomers. Each pair of enantiomers should function equivalently except with respect to the sign of polarization, as noted above.

The substituted phenols, R′—Ar—OH, employed for the preparation of the compounds of formulas I-VII are either commercially available or can be prepared by methods known to the art. Descriptions in the examples and Schemes V-XIV provide guidance for the synthesis of compounds having selected Ar core units.

Methyleneoxy (—CH$_2$—O—) and methylenethio (—CH$_2$—S—) linkages can be readily substituted for a carbonyloxy in connecting two aromatic rings or heteroaromatic rings of the present invention in the synthesis of cores of the present invention. This can be accomplished by reduction of a corresponding aromatic acid to the alcohol, conversion of the alcohol to a leaving group such as a bromide or tosylate, and coupling with an appropriate phenol or thiophenol as shown below, where M and/or N, independently of one another are: a 1,4-substituted phenyl ring, a 2,5-substituted pyridine ring, a 2,5-substituted pyrimidine ring, a 3,6-substituted pyridizine ring, a 2,5-substituted pyrazine ring, or two ring combinations thereof:

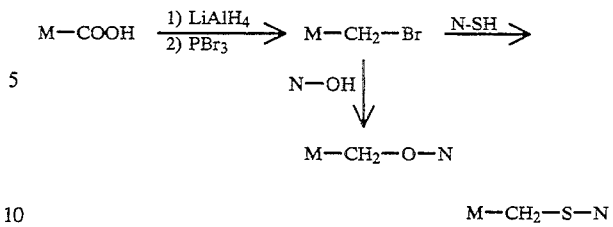

Ethylene linkages can be introduced into aromatic ring cores of the present invention via the reduction of corresponding tolanes, for example, by hydrogeneration with a Palladium/Carbon catalyst. Tolanes having aromatic rings of the cores of the present invention can be synthesized by methods described in Pugh et al. (1990) Mol. Crys. Liq. Crys. 178:193-217 or by routine adaptation of those methods in view of the disclosures herein.

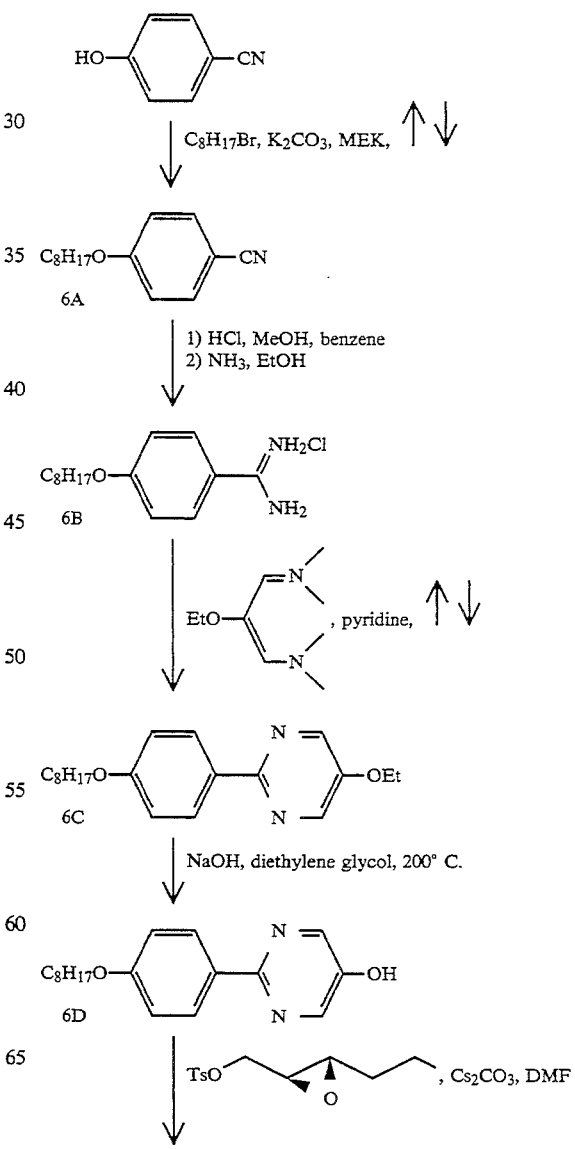

5,380,460
-continued
SCHEME V
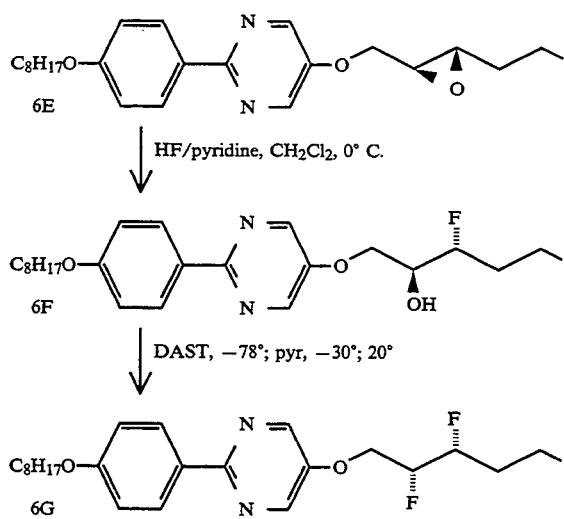
-continued
SCHEME VII
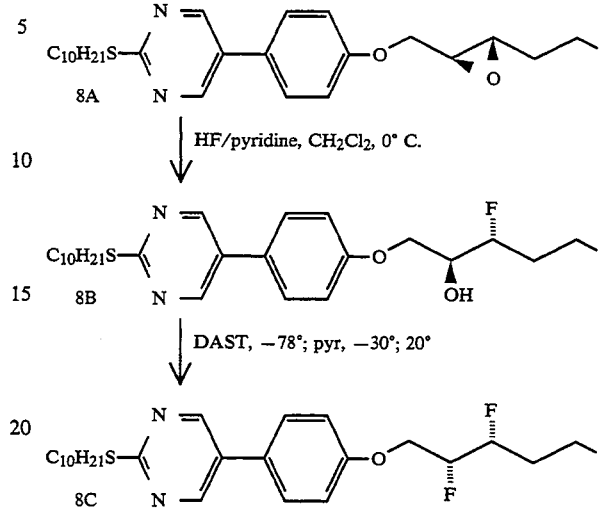
SCHEME VI
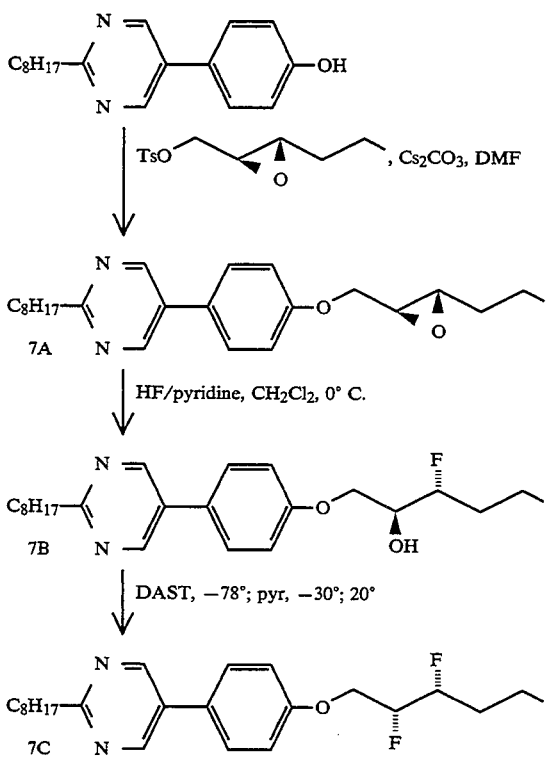
SCHEME VIII
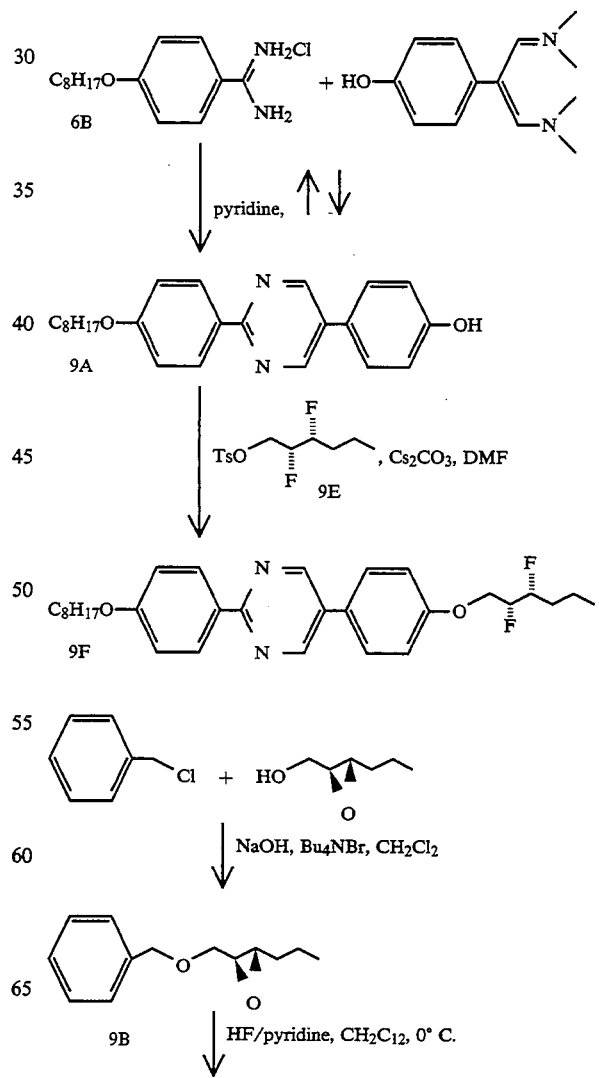
SCHEME VII
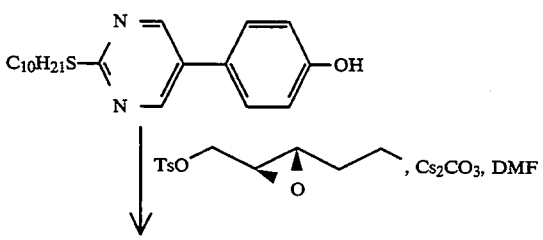

-continued
SCHEME VIII
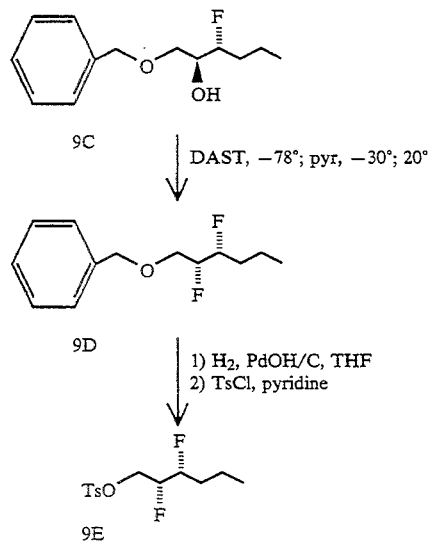
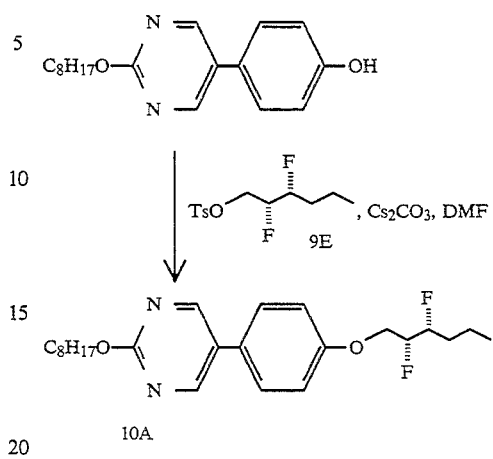
SCHEME IX
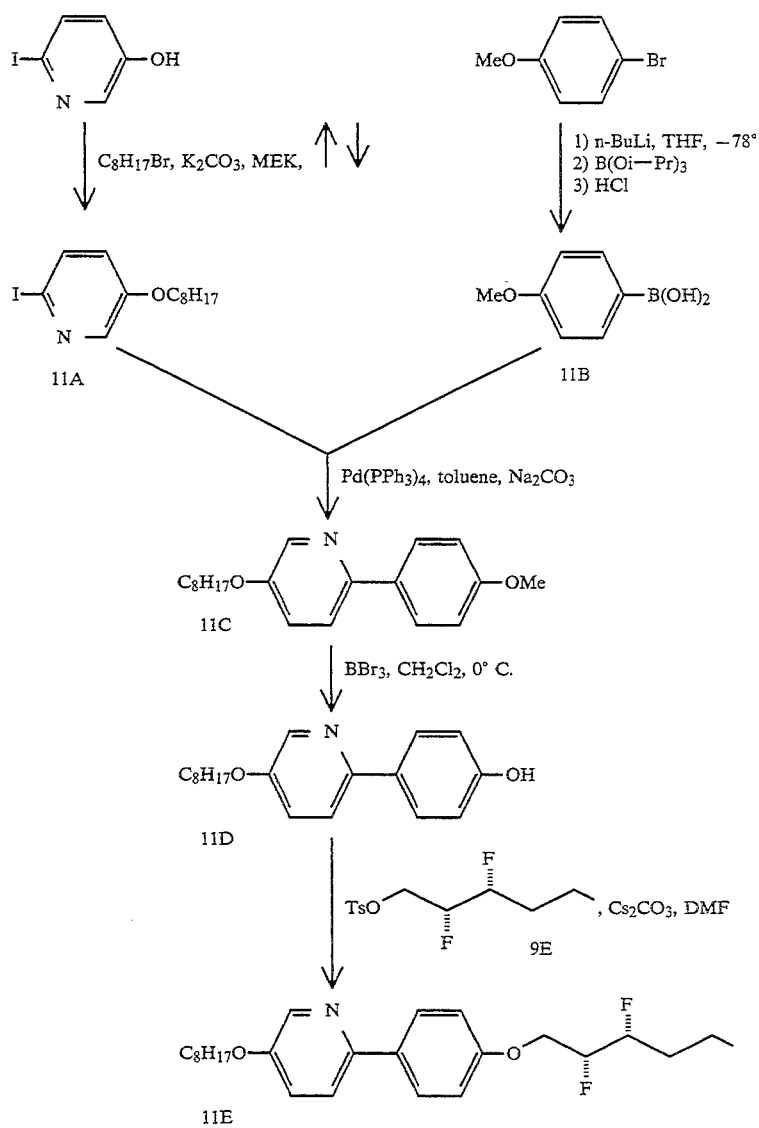

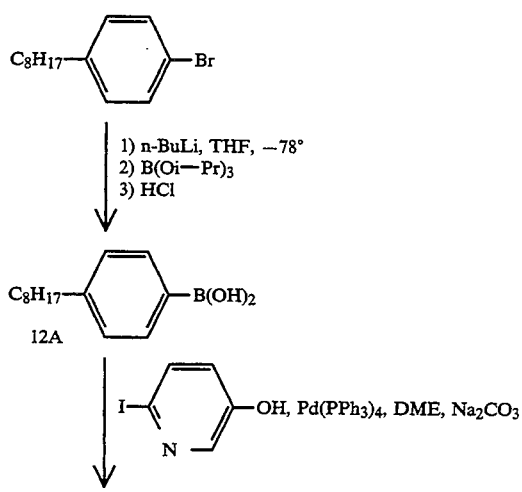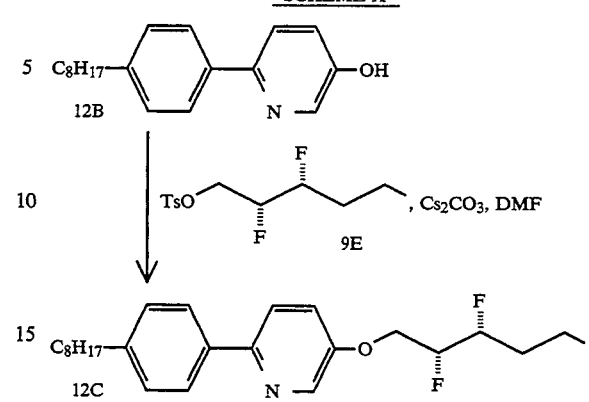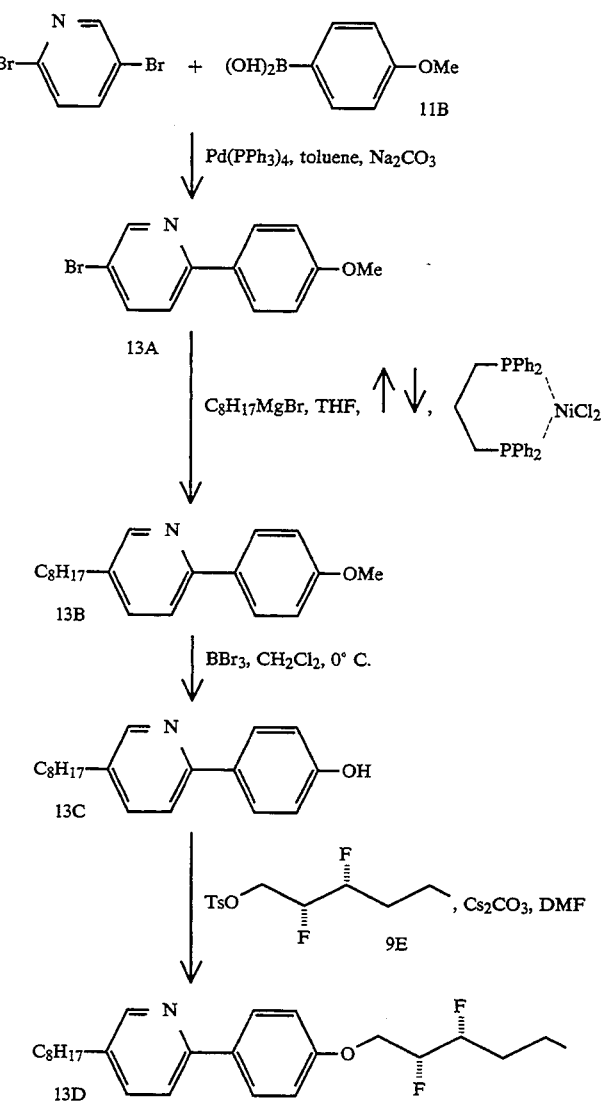

SCHEME XI
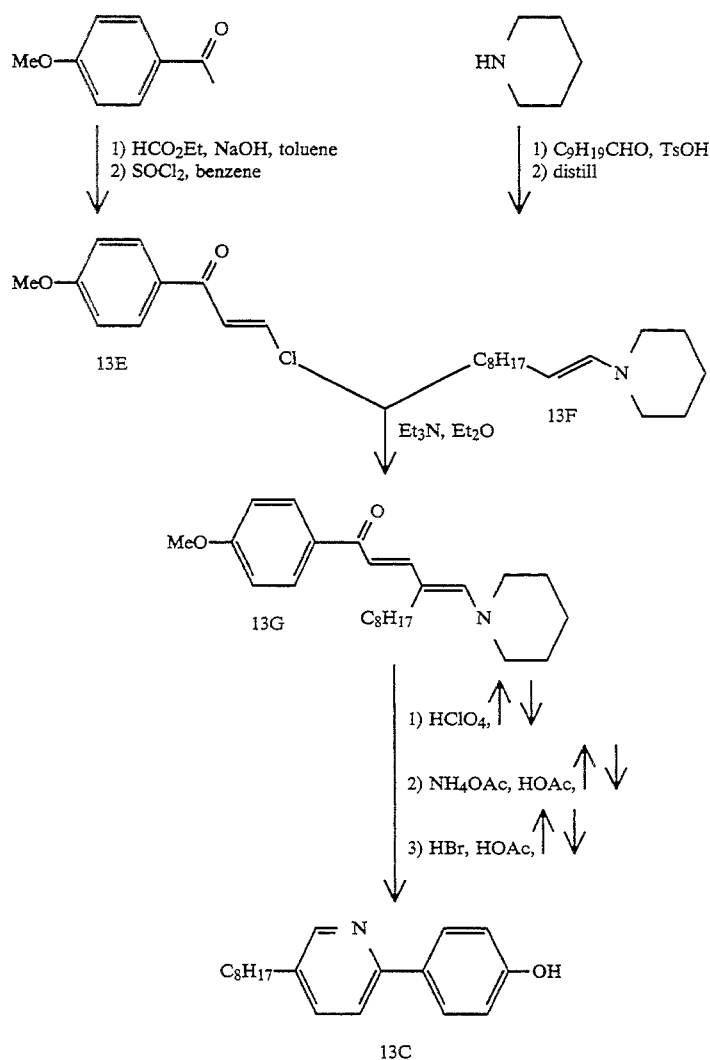
SCHEME XII
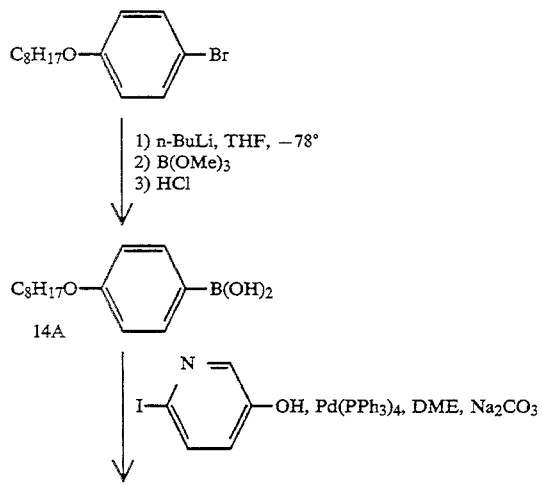
-continued
SCHEME XII
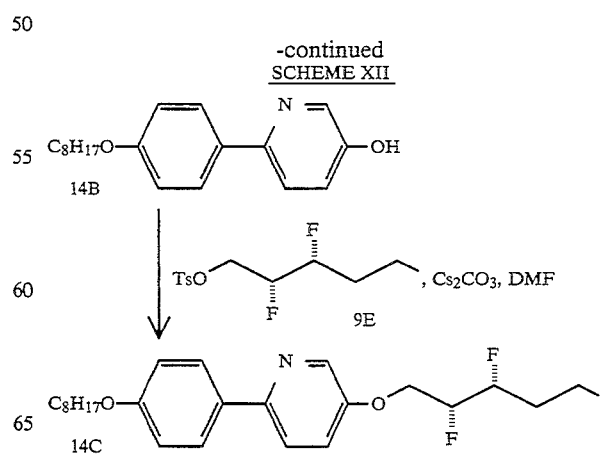

SCHEME XIII

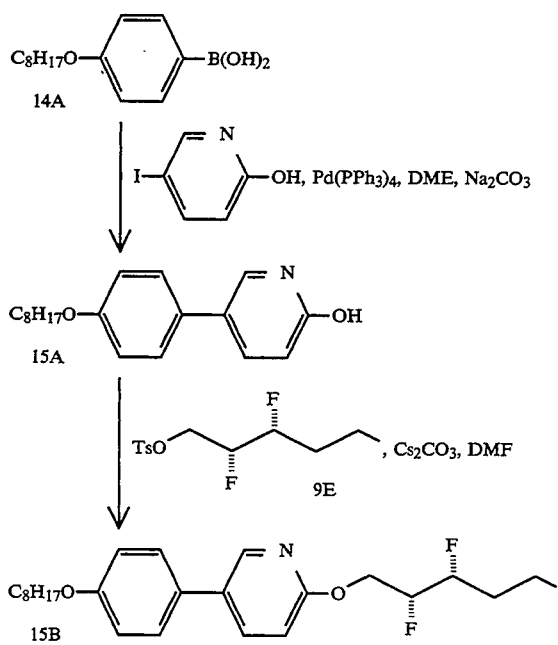

SCHEME XIV

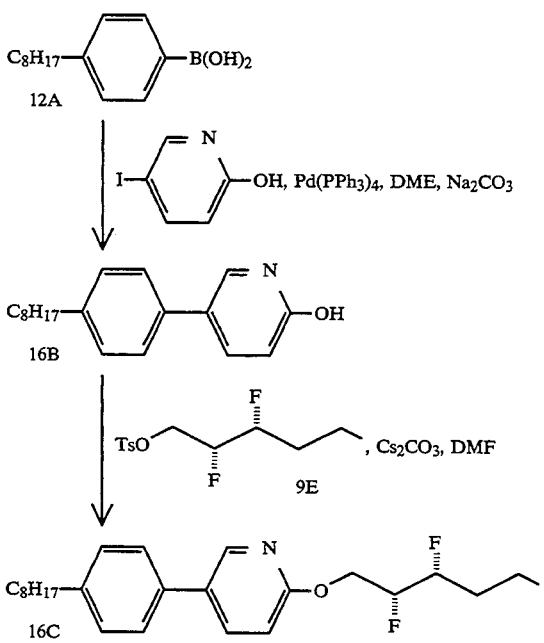

The synthesis of thiadiazoles of the structure:

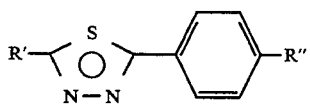

where R' and R" are alkyl, alkoxy, a chiral nonracemic group, a phenyl ring or nitrogen containing aromatic ring, including those of the present invention, can be performed as described in published European patent application 89105489.2. The methods described therein can be readily adapted to synthesis of the compounds of the present invention. The chiral nonracemic tails of the present invention, including the 2,3-difluoroalkoxy tail, can be attached to the thiadiazole core by conventional methods or as described herein.

Thialkyl, thioether, ether and alkenyl R' and/or R groups can be readily introduced by routine adaptation into the aromatic cores of the present invention in view of the disclosures herein.

Dialkylsilyl groups can be introduced into R' tails employing known methods, for example as described in EP application 355,008 published Feb. 21, 1990.

The liquid crystal properties of the compounds of formula I are exemplified by those of the 2R,3R dichloroalkoxyphenylbenzoate (I, where X=Y=Cl, R'=n-decyloxy, R=n-propyl and Ar=4,4'-phenylbenzoate) which is designated MDW 32, the 2R, 3R difluoroalkoxy-phenylbenzoate (I, where X=Y=F, R'=n-decyloxy, R=n-propyl and Ar=4,4'-phenylbenzoate) which is designated MDW 86, and those of the regioisomers 2R-fluoro, 3R-chloroalkoxyphenylbenzoate (I, where X=F, Y=Cl, R'=n-decyloxy, R=n-propyl and Ar=4,4'-phenylbenzoate) designated MDW 89 and 2R-chloro, 3R-fluoroalkoxyphenylbenzoate (I, where X=Cl, Y=F. R'=n-decyloxy, R=n-propyl and Ar=4,4'-phenylbenzoate) designated MDW 88. The liquid crystal properties of the compounds of formula II are exemplified by those of the 2R,3S difluoroalkoxyphenylbenzoate (II, where X=Y=F, R'=n-decyloxy, R=n-propyl and Ar=4,4'-phenylbenzoate) which is designated MDW 84. The liquid crystal properties of (2R, 3R) difluoroalkoxy FLC compounds having two and three aromatic ring cores are exemplified by those in Table 3.

The structures of (2R,3R) difluorohexyoxy FLC compounds with varying cores are presented in Table 4 with identifying MDW numbers.

The compounds MDW32, MDW 86, MDW 89, MDW 299, MDW 455 and MDW 456, in pure form, do not possess an enantiotropic or monotropic ferroelectric liquid crystal phase. The compounds MDW 84 and MDW 88, in pure form, possess a monotropic smectic C* phase, possibly a C phase, that appears to be switchable. The optical contrast of these phases is too low, however, to allow measurement of switching speeds. The low optical contrast of these phases suggests that the tilt angle of the phases is either high (approaching 45°) or low (approaching 0°). MDW 405, MDW 453 and MDW 454 in pure form display smectic C* phases.

All the compounds listed in Tables 2 and 3 can be mixed with known FLC host materials to give mixtures having a smectic C* phase. When any of the compounds MDW 32, MDW 84, MDW 86, MDW 88 or MDW 89 are mixed with a known FLC host material, such as W82, mixtures possessing ferroelectric smectic C* phases are produced.

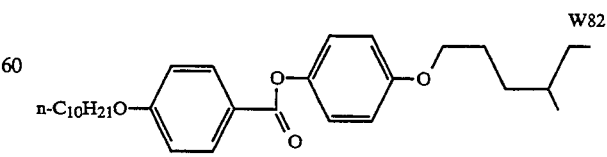

Tables 2 and 3 summarize the phase transition temperatures, optical rise times and polarization densities of some exemplary mixtures of FLC dopants of the present invention. In the Tables, the phases are noted as X=crystal, I=isotropic liquid, A=smectic A, C*=smectic C, N*=chiral nematic, $S_x$ is unspecified smectic and phase transition temperatures are given in °C. Optical rise times are measured in response to a driving voltage of 15 V/μm at the temperature given in the table. Polarization densities (P) are given in $nC/cm^2$ and the magnitude of P was measured by integration of the dynamic current response on reversing the applied electric field, as described in Martinot-Lagarde (1976) J. Phys. 37, C-3, p. 129 and Martinot-Lagarde (1977) J. Phys. Lett. 38, L-17.

W82 is known to possess an enantiotropic ferroelectric C* phase with very low polarization density of <0.5 $nC/cm^2$ and slow electro-optical switching speed of the order of 3 msec (1 μm thick layer, SSFLC geometry, 15 V/μm driving voltage). Mixtures of the compounds of the present invention, particularly compounds as shown in Table 2, possess ferroelectric C* phases with higher polarization density and/or faster switching speeds than W82.

TABLE 2

Properties of FLC Mixtures

| Mixture | Phase Sequence[1] | $\tau\tau$ μsec | Temp. °C. | P $nC/cm^2$ |
|---|---|---|---|---|
| MDW32 + W82 (1:1) | X<—O-I*<—15—C*<—45—A<—5-7—I | 68 | 30 | 85 ($P_{ex}$ = 170) |
| MDW84 + W82 (10%) | X<—C*<—58—A<—77—I | 400 | 30 | 0.9 ($P_{ex}$ = 9.0) |
| MDW86 + W82 (10%) | LX<—C*<—74—A<—78—I | 60 | 30 | 12.0 ($P_{ex}$ = 120) |
| MDW88 + W82 (10%) | X<—C*<—66—A<—73—I | 300 | 55 | |
| MDW89 + W82 (10%) | X<—$S_x$<—30—C*<—67—A<—72—I | 46 | 39 | |

[1]transition temperatures are in °C.

TABLE 3

Properties of some difluoroalkoxy compounds

| MDW # | conc, mix | Θ | $P_{ext}$ | $\tau^c$ 10–90° | $\tau^c$ 0–90° | Mesomorphic Properties | Phase Diagram of Mixture |
|---|---|---|---|---|---|---|---|
| 234 | | | | | | I →172°→ N ⇌117°/125° A →95°→ X | |
| 299 | 10%[a] | | 249 | 45 | 88 | I ⇌80°/90° X | I →84°→ N →74°→ A →62°→ C →≤RT→ X |
| 405 | 10%[b] | 28° | 310 | 25 | 48 | I →98°→ N ⇌90°/92° C →88°→ X | |
| 428 | 10%[a] | 25° | 137 | 41 | 68 | I ⇌100° $S_x$ ⇌92° X | I →86°→ N →75°→ A →61°→ C →≤RT→ X |
| 429 | 10%[a] | 26° | 203 | 87 | 126 | I →98°→ N ⇌92°/96° X | I →85°→ N →73°→ A →66°→ C →≤RT→ X |
| 451 | 5%[b] | 21° | 128 | 52 | 124 | I →98°→ A ⇌60°/88° X | I →91°→ N →87°→ A →67°→ C →≤RT→ X |
| 453 | 5%[b] | 22.5° | 188 | 38 | 92 | I →195°→ A →176°→ C ⇌125°/140° X | I →96°→ N →89°→ A →74°→ C →≤RT→ X |
| 474 | 10%[b] | 23° | 59 | 42 | 87 | I ⇌76°/80° A →63°→ X | I →88°→ A →58°→ C →≤RT→ X |
| 454 | 5%[b] | 21° | 138 | 45 | 97 | I ⇌80°/87° A →79°→ C →76°→ X | I →90°→ N →86°→ A →63°→ C →≤RT→ X |
| 455 | | | | | | I →≤−20°→ X | |
| 456 | | | | | | I →≤−20°→ X | |

TABLE 3-continued

Properties of some difluoroalkoxy compounds

| MDW # | conc, mix | Θ | $P_{ext}$ | $\tau^c$ 10–90° | $\tau^c$ 0–90° | Mesomorphic Properties | Phase Diagram of Mixture |
|---|---|---|---|---|---|---|---|
| 331 | | | | | | I $\xrightarrow{57°}$ N $\xrightarrow{28°}$ C $\xrightarrow{26.5°}$ X | |

<sup>a</sup>This host mixture has the phase diagram I $\xrightarrow{85°}$ N $\xrightarrow{77°}$ A $\xrightarrow{63.5°}$ C $\xrightarrow{\leq RT}$ X <sup>b</sup>This host mixture has the phase diagram I $\xrightarrow{90°}$ N $\xrightarrow{84°}$ A $\xrightarrow{69°}$ C $\xrightarrow{\leq RT}$ X <sup>c</sup>The rise time, given in μs, was measured at 8.6 V/μm and extrapolated to 15 V/μm.

TABLE 4

| Structure | MDW # |
|---|---|
| $C_6H_{13}$—[pyrimidine]—[phenyl]—C(O)O—[phenyl]—OR* | 234 |
| $C_8H_{17}$—[pyrimidine]—[phenyl]—OR* | 299 |
| $C_{10}H_{21}O$—[phenyl]—[pyrimidine]—OR* | 405 |
| $C_8H_{17}O$—[pyrimidine]—[phenyl]—OR* | 428 |
| $C_8H_{17}O$—[phenyl]—[pyrimidine]—OR* | 429 |
| (branched chiral chain)—O—[pyrimidine]—[phenyl]—OR* | 331 |
| $C_8H_{17}O$—[pyrimidine]—[phenyl]—OR* | 451 |
| $C_8H_{17}O$—[phenyl]—[pyrimidine]—[phenyl]—OR* | 453 |
| $C_{10}H_{21}S$—[pyrimidine]—[phenyl]—OR* | 474 |
| $C_8H_{17}$—[pyrimidine]—[phenyl]—OR* | 454 |

TABLE 4-continued

| Structure | MDW # |
|---|---|
| $C_8H_{17}$—[pyridine]—[phenyl]—OR* | 455 |
| $C_8H_{17}O$—[phenyl]—[pyridine]—OR* | 456 |

An important aspect of the present invention is the finding that the dihaloalkoxides of formula I have properties as FLC dopants significantly different from those of formula II. Compounds of formula I can impart higher polarization densities in FLC mixtures. This property can be qualitatively compared in the different diastereomers by comparing the polarization densities the pure diastereomers would have if they possessed a C* phase, which can be approximately determined by extrapolation from polarization density measurements in mixtures. This difference can be discerned physically, since FLC mixtures containing the I isomer will display higher polarization densities (E), and faster switching speeds than FLC mixtures containing an equal amount of the corresponding II isomer. It is believed that the difference in polarization densities of I and II isomers is due to the relative alignment of the halogen bond dipoles in the preferred conformation of the isomers within the FLC phase. In the I isomers, the dipoles are aligned in the same direction with respect to the smectic tilt plane, while in the II isomers the dipoles are opposed, resulting in the higher polarization density of the I isomer. The relationship between dipole alignment and ferroelectric polarization density has been discussed for related molecules in Walba et al. (1986a), and Walba et al. (1986b), supra. The difference in polarization between isomers of formula I and II is general, dependent on the preferred configuration of the molecule in the liquid crystal phase, but qualitatively independent of X and the structure of the core.

An unanticipated result of the present invention was the finding that the regioisomers of formula I (when X is not equal to Y) can have significantly different properties in an FLC phase. In particular, the isomer in which a fluorine is at the two position, closer to the core linkage, confers a considerable faster switching speed than its analogous regioisomer, in which fluorine is at the three position (see Table 2). The reason for the difference in properties of the regioisomers is not fully understood. The faster switching speeds associated with the 2-fluoro isomers could result from either a lower orientational viscosity or a higher polarization of these isomers.

The high polarization of the monohalides of formula IV are believed to derive from the alignment of the alkoxy oxygen and the halogen bond dipoles in the FLC phase. This alignment can be achieved when the 2-haloalkoxy tail is directly linked to the core unit, by an ether linkage. Similar dipole alignment might not be achieved if, for example, the monohalide alcohol tail was indirectly linked to the core, for example by an ester linkage, due to changes in preferred configuration of the tail imposed by the modified linkage and to the presence of other nearby dipoles.

The differences observed between the dihalide diastereomers of formulas I and II indicate that the diastereomeric trihalides (IV–VII) have similar differences in ferroelectric properties. By analogy with the compounds of formula I, compounds of formula IV in which the three halide bond dipoles are aligned with the alkoxy oxygen bond dipole in the preferred configuration are expected to have higher polarization densities, and to effect faster switching speeds than their diastereomers (V–VII).

Variation in the structure of the cores and length and degree of branching in the R and R' groups of compounds encompassed in formulas I–VII can affect the liquid crystal properties of the pure material or mixtures containing them. For example, some of the compounds of the present invention may possess smectic C* phases while others do not and the characteristics of any such smectic C* phases (i.e., stability, temperature range) may vary. For example, addition of a compound of the present invention to an FLC mixture can result in a broadening of an existing smectic C* phase or the introduction of a new phase. Furthermore, the optical switching speed is also affected by the orientational viscosity of the liquid crystal. The structure of the core as well as the size and branching of the R and R' groups can affect viscosity. For example, it is expected that compounds of the present invention having phenylpyrimidine cores will show faster switching speeds than their phenylbenzoate and biphenyl analogs due to a lower orientational viscosity associated with the phenylpyrimidine core unit.

EXAMPLES

EXAMPLE 1

Synthesis of Phenylbenzoate Epoxides

Chiral nonracemic phenylbenzoate (2,3) epoxides (VIII and X, trans and cis isomers, respectively, where Ar is 4,4'-phenylbenzoate) were synthesized by a modification of the methods described in Walba and Vohra, U.S. Pat. No. 4,638,073. The epoxides are prepared by initial coupling of 4-benzyloxyphenol with an appropriate chiral epoxy bromide, followed by debenzylation of the resulting coupling product and finally by coupling of the resulting substituted phenol with an appropriately substituted alkyl or alkoxy benzoyl chloride:

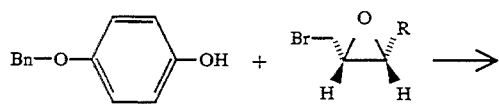

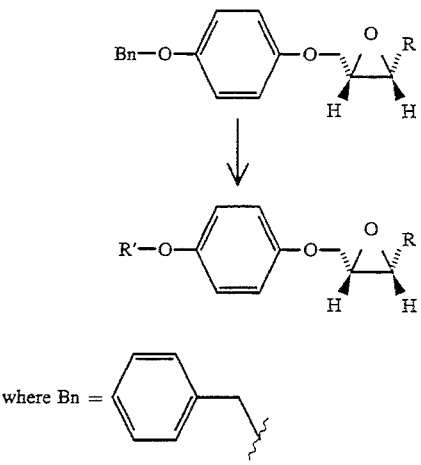

The epoxy bromides were prepared from the chiral epoxy alcohols described in Walba and Vohra, supra. This example illustrates the procedures for synthesis of phenylbenzoate epoxides by detailing the synthesis of the trans epoxide, 4-[(2S,3S)-epoxy]hexyloxyphenyl-4'-decyloxybenzoate (VIII, where R'=n-decyloxy and R=n-propyl).

p-Toluenesulfonyl chloride (67.58 g, 0.355 mol) was introduced into a 1 l flame-dried round bottom flask along with 105 ml each of anhydrous THF and dry pyridine. The mixture was stirred until the chloride was dissolved. The resulting solution was cooled to 0° C., after which a solution of (2S,3S)-3-propyloxiranemethanol (39.17 g, 0.338 mol) in 50 ml anhydrous THF was added dropwise. The reaction mixture was then stirred for 18 hr at 5° C. The reaction mixture was then partitioned between water and ethyl ether. The ether layer was removed, washed with dilute HCl and dried with anhydrous MgSO$_4$. Removal of solvent in vacuo gave a pale yellow, oily solid. This material was recrystallized from hexanes affording 70.82 g (72%) of white crystals, the tosylate of (2S,3S)-3-propyloxiranemethanol.

The tosylate (10.8 g, 40 mmol) in 110 ml of anhydrous THF was introduced into a flame-dried 250 ml round bottom flask. Anhydrous LiBr (13.92 g, 160 mmol) was then added to the solution and the reaction mixture was stirred at ambient temperature for 72 hr. THF was then removed from the mixture and the resulting residue was partitioned between water and ether. The ether layer was washed with water, and dried with anhydrous MgSO$_4$. Removal of solvent, at 25° C., 30 torr gave 4.82 g (67%) of 1-bromo-(2R,3S)-epoxyhexane as a clear liquid.

4-Benzyloxyphenol (2.0 g, 10.0 mmol) in 50 ml anhydrous THF was added to a 100 ml flame-dried round bottom flask equipped with a condenser. NaH (240 mg, 10.0 mmol) was then added to the flask, after which a solution of 1-bromo-(2S,3S)-epoxyhexane (1.43 g, 8.0 mmol) in anhydrous DMF (10 ml) was added. The resulting reaction mixture was refluxed for 2 hr, after which it was partitioned between water and ether. The ether layer was washed with water and dried with anhydrous MgSO$_4$. Removal of solvent in vacuo, followed by flash chromatography (15% (v/v) ethyl acetate/hexanes) of the residue resulted in 2.01 g (88%) of 4-benzyloxy-1-[(2S,3S)-epoxy]-hexyloxybenzene.

4-Benzyloxy-1-[(2S,3S)epoxy]hexyloxybenzene (0.67 g, 2.2 mmol), 5 ml of ethanol and 100 mg of 10% Pd on carbon was added to a glass hydrogenator equipped with a magnetic stir bar. The reaction vessel was then evacuated and hydrogen was introduced. The mixture was allowed to stir for 3–4 hr under a positive pressure of hydrogen until the reaction was complete. The reaction was judged complete by TLC; the product having an Rf=0.28 on elution with 7/3 (v/v) hexanes/ethyl acetate. The product, 4-[(2S,3S)-epoxy]hexyloxyphenol (0.35 g), was purified by chromatography employing the same eluent.

To a 10 ml flask equipped with a magnetic stir bar and charged with 4-[(2S, 3S)-epoxy]-hexyloxyphenol (97 mg, 0.5 mmol) was added dry $CH_2Cl_2$ (2 ml), 0.5 ml of triethylamine and a few crystals of DMAP. p-Decyloxybenzoyyl chloride (148 mg, 0.5 mmol) in 1 ml of dry $CH_2Cl_2$ was then added to the flask. The resulting mixture was stirred for 1 hr., after which the solvent was removed. The residue was treated with aqueous HCl (5%, v/v) followed by extraction with ether (2×25 ml). The combined ether layers were washed sequentially with 5% aqueous HCl, 5% aqueous NaOH (2x), and water and then dried over anhydrous sodium sulfate. Removal of solvent gave 0.22 g of crude product, 4-[(2S,3S)-epoxy]hexyloxyphenyl-4'-decyloxybenzoate (VIII, where R'=n-decyloxy and R=n-propyl), which was then purified by flash chromatography using 9/1 (v/v) hexanes/ethyl acetate as eluent. The product can be further purified by recrystalization from ethanol.

EXAMPLE 2

Synthesis of Chiral Nonracemic 2,3-dihaloalkoxy Phenylbenzoates

This example illustrates the synthesis of chiral 2,3-dihaloalkoxyphenylbenzoates by stereospecifc (or selective) halogenation of chiral phenylbenzoate epoxides. These syntheses proceed through 2,3-halohydrin intermediates. The procedure is illustrated by the synthesis of the dichloride, 4- (2R, 3R-dichloro-1-hexyloxy)-4'-decyloxyphenylbenzoate (I, where R'=n-decyloxy, R=n-propyl and X=Y=Cl), the difluoride, 4-(2R,3R-difluoro-1-hexyloxy)-4'-decyloxyphenylbenzoate (I, where R'=n-decyloxy, R=n-propyl and X=Y=F) and both of the corresponding 2,3 chlorofluoro regioisomers, 4-(2R-chloro-3R-fluoro-1-hexyloxy)-4'-decyloxyphenylbenzoate (I, where R'=n-decyloxy, R=n-propyl, X=Cl and Y=F) and 4-(2R-fluoro-3R-chloro-1-hexyloxy)-4'-decyloxyphenylbenzoate (I, where R'=n-decyloxy, R=n-propyl, X=F and Y=Cl).

2a: 4-(2R, 3R-dichloro-1-hexyloxy)-4'-decyloxyphenylbenzoate.

To a 50 ml flame-dried round bottom flask equipped with a magnetic stir bar 4-[(2S,3S)-epoxy]-hexyloxyphenyl-4'-decyloxybenzoate (1.87 g, 4.4 mmol) in 15 ml dry THF was added. Lithium chloride (860 mg, 6.4 mmol) and cupric chloride (542 mg, 12.8 mmol) were then added to the solution and the resulting mixture was stirred for 10 minutes at ambient temperature. To the resulting dark brown homogeneous solution, a 1.0 M ethereal solution of hydrogen chloride (12.0 ml, 12 mmol) was added. The reaction mixture was then stirred for 18 hours at ambient temperature.

The reaction mixture was worked up with ethyl ether to give 2.07 g of a white solid. TLC of the crude reaction product showed the presence of both chlorohydrin regioisomers. Flash chromatography (7/10/83, v/v/v, $EtOAc/CH_2Cl_2$/Hexanes) afforded 1.524 gm (76%) of pure product, 4-(2S-hydroxy-3R-chloro-1-hexyloxy)-4'-decyloxyphenylbenzoate.

To a 50 ml flame-dried round bottom flask equipped with an argon inlet, a magnetic stir bar and a condenser was added 4-(2S-hydroxy-3R-chloro-1-hexyloxy)-4'-decyloxyphenylbenzoate (505 mg, 1.0 mmol) in 15 ml dry THF. Dry pyridine (1.6 gm, 20 mmol) and thionyl chloride (357 mg, 3.0 mmol) were then added and the reaction mixture was refluxed for 4 hours. Ethereal extractive work up and flash chromatograph (3% (v/v) ethyl acetate/hexanes) afforded 342 mg (67%) of the product, 4-(2R,3R-dichloro-1-hexyloxy)-4'-decyloxyphenylbenzoate as a white solid.

Since this chlorine substitution reaction proceeds with inversion of configuration at the hydroxyl carbon of the chlorohydrin, only the single product 4-(2R,3R-dichloro-1-hexyloxy)-4'-decyloxyphenylbenzoate will result on chlorination of the mixture of chlorohydrin regioisomers (see Scheme I). Separation of the chlorohydrin regioisomers prior to the chlorine substitution reaction is therefore not necessary.

2b: 4-(2R, 3R-difluoro-1-hexyloxy)-4'-decyloxyphenylbenzoate.

To a 50 ml polyethylene bottle 4-[(2S,3S)-epoxy]-hexyloxyphenyl-4'-decyloxybenzoate (1.95 g, 4.17 mmol) in 10 ml of dry $CH_2Cl_2$ was added. The reaction solution was then cooled to 0° C., after which 5 ml of $(HF)_x$·pyridine was added and the resulting mixture was stirred for 15 min. The reaction was then quenched by addition of 50 ml of water. Ethereal extractive workup resulted in 1.95 g of a white solid. Flash chromatography of this material (ethyl acetate/hexanes, 15%, v/v) afforded 1.32 g (65%) of a white solid which was a mixture of fluorohydrin regioisomers.

The mixture of fluorohydrin regioisomers (614 mg, 1.26 mmol) in 10 ml of dry $CH_2Cl_2$ was introduced into a 50 ml flame-dried round bottom flask. The solution was then cooled to −78° C., under argon. Diethylamino sulfurtrifluoride, DAST, (175 μl) was added dropwise to the cooled solution which was then stirred for 10 min. The cooling bath was removed after which the reaction mixture was stirred for an additional hour. The reaction was then quenched with 10% (w/v) sodium bicarbonate. A milky white solid was obtained by ethereal extractive workup of the reaction mixture. The product was a mixture of diastereomers: the 2R,3R-difluoro and the 2R,2S-difluoro isomers. The diastereomeric difluorides were separated and purified by flash chromatography (ethyl acetate/hexanes, 8%, v/v) in two fractions. The first fraction (175 mg) was the 2R,3S-difluoride. The second fraction (230 mg) was the 2R,3R-difluoride.

2c: 4-(2R-chloro-3R-fluoro-1-hexyloxy)-4'-decyloxyphenylbenzoate and 4-(2R-fluoro-3R-chloro-1-hexyloxy)-4'-decyloxyphenylbenzoate.

The mixture of fluorohydrin regioisomers (600 mg, 1.23 mmol), prepared as in Example 2b, in 15 ml dry THF was introduced into a 50 ml flame-dried round bottom flask equipped with an argon inlet and a condenser. A mixture of thionyl chloride (357 mg, 3.0 mmol) and dry pyridine (800 mg, 10 mmol) was then added to the flask, after which the reaction mixture was refluxed for 4 hr. Ethereal extractive workup of the reaction mixture, followed by gradient elution flash chromatography (1% to 3% v/v, ethyl acetate/hexanes) afforded two major fractions. The first fraction contained 182 mg of the 2R-fluoro-3R-chloro isomer and the second fraction contained 342 mg of the 2R-chloro-3R-fluoro isomer.

A mixture of the 2R-fluoro-3R-chloro and 2R-chloro-3R-fluoro regioisomers can also be prepared by reaction of the chlorohydrin regioisomers, see Example 2a, with DAST fluorination reagent. However, since the DAST reaction proceeds with partial retention of configuration at the hydroxy carbon, two other chloro, fluoro isomers, 4-(2R-chloro-3S-fluoro-1-hexyloxy)-4'-decyloxphenylbenzoate and 4-(2S-fluoro-3R-chloro-1-hexyloxy) -4'-decyloxyphenylbenzoate are produced.

EXAMPLE 3

Synthesis of Chiral Dihaloalkoxy Phenylpyrimidines.

The chiral 2,3 dihaloalkoxyphenylpyrimidine compounds of formulas I and II (where Ar is 5,4'-phenylpyrimidine) are prepared from the chiral 2,3 epoxy phenylpyrimidines (VIII and X, where Ar=5,4'-phenylpyrimidine) using methods analogous to those employed in Example 2.

Chiral phenylpyrimidine epoxides have been prepared by the coupling of substituted pyrimidine phenol with an appropriate chiral bromoepoxide:

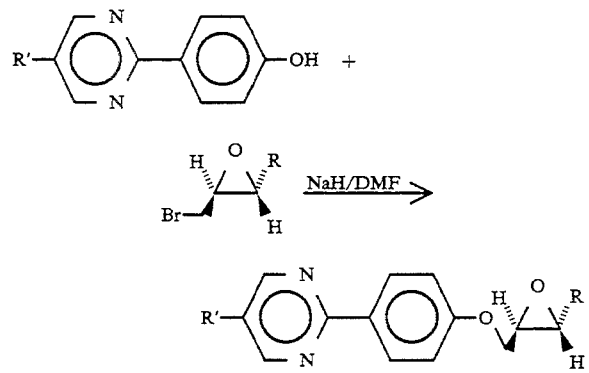

The procedure is illustrated by the preparation of 2-(4'-(3-n-propyl(2S,3S-epoxymethyleneoxyphenyl)-5-decylpyrimidine. A solution of 5-decylpyrimidine-4'-phenol (505 mg, 1.62 mmol) in 10 ml anhydrous THF was introduced into a 50 ml round bottom flask equipped with a condenser. NaH (40 mg, 1.60 mmol) was then added to the flask, after which a solution of 1-bromo-2R,3S-epoxyhexane in 2 ml anhydrous DMF was added. The resulting reaction mixture was refluxed for 2 hr. The reaction mixture was then partitioned between water and ether. The ether layer was washed with water and dries with anhydrous MgSO4. Removal of the solvent in vacuo gave 647 mg of an off-white solid. Flash chromatography (8%, v/v, ethyl acetate/hexanes) of this material followed by recrystalization from hexanes afforded 485 mg of 2-(4-(3-n-propyl)-2S,3S-epoxymethyleneoxyphenyl)-5-decylpyrimidine.

The substituted pyrimidine phenols are prepared by known methods, such as those described in A. Boller et al. (1978) Z. Naturforsch. 33b:433–438.

EXAMPLE 4

Synthesis of Chiral Dihaloalkoxybiphenyls

The chiral 2,3 dihaloalkoxybiphenyl compounds of formulas I and II (where Ar is 4,4'-biphenyl) are prepared from the chiral 2,3 epoxy biphenyls (VIII and X , where Ar=4,4'-biphenyl) using methods analogous to those employed in Example 2.

The preparation of chiral 2,3 epoxy biphenyls has been described in Walba and Vohra, supra. However, these compounds can also be prepared as described in Examples 1 and 3 by coupling of substituted biphenyl phenols with chiral epoxy bromides. The procedure is illustrated by the synthesis of 4-(3-n-propyl-2S,3S-epoxymethyleneoxy)-4'-decyloxybiphenyl.

A solution of 4'-decyloxy-4-hydroxybiphenyl (342 mg, 1.05 mmol) in anhydrous THF (10 ml) was introduced into a 50 ml round bottom flask equipped with a condenser. NaH (24 mg, 1.00 mmol) was then added to the flask, after which a solution of 1-bromo-2R,3S-epoxyhexane (263 mg, 1.05 mmol) in 2 ml of anhydrous DMF was added. The reaction mixture was then refluxed for 2 hr, after which the reaction mixture was partitioned between water and ether. The ether layer was washed with water, and then dries with anhydrous MgSO4. Removal of the solvent in vacuo resulted in 397 mg (80%) of epoxide VIII, where Ar=4,4'-biphenyl, R'=n-decyloxy and R=n-propyl.

EXAMPLE 5

Synthesis of Chiral Trihalo Alcohols

The chiral trihalo alcohol intermediates are prepared employing the chiral acetonide of glyceraldehyde and an appropriate Wittig reagent by the method of Scheme III. Alternatively, certain of the chiral trihalo alcohol intermediates (those in which X=Y=Z) can be prepared by the method of Scheme IV starting with an appropriate nonracemic sugar. Both methods are exemplified by the preparation of the 2S,3S,4R trifluoro alcohol, where R is n-butyl.

In the method of Scheme III, (R)-glyceraldehyde acetonide is treated by the regioselective Schlosser-Wittig trans olefination method, employing Ph3P, n-pentyl bromide (or other halogen) and base (i.e. PhLi) and the product is deprotected with acid. The primary alcohol of the resulting trans-olefin diol is selectively protected with trimethylacetyl chloride. Afterwhich the olefin bond of the protected alcohol is steroselectively epoxidized with meta-chloroperbenzoic acid. The resulting epoxy alcohol is fluorinated by initial treatment with mesylchloride/pyridine followed by displacement with KF/18-Crown-6, for example, to give the inversion product, 2(S)fluoro, 3(R)4(R) epoxide. The fluoro epoxide is then treated with HF/pyridine or DAST, with double inversion, to obtain 2(S),3(S),4(R) trifluorononanol, where X=Y=Z and R=n-butyl. Any diasteromeric trifluoro alcohols produced by retention of configuration on halogenation are separated by conventional chromatographic methods.

In the alternative method of Scheme IV, α-methyl D-glucopyranoside is employed as the starting chiral sugar. The sugar is treated with trityl chloride or any other such primary alcohol selective, acid-sensitive protecting group. The remaining free hydroxyl groups of the sugar are then protected for example by acetylation and the resulting protected sugar is treated with acid to produce a hemiacetal. Protection of the aidehyde, for example by Wittig olefination, followed by cleavage of the 1,2-diol with an oxidizing agent such as RuO4 and reduction of the resulting aldehyde with a mild reducing agent, such as NaCNBH3 gives the protected alcohol. Tosylation and alkylcuprate coupling with lithium di(n-butyl)cuprate gives the chiral tri-protected alkene. Removal of the protecting groups with mild base or a reducing agent, such as LAH, followed by stereoselective fluorination with DAST reagent, for example, resulting in inversion gives the chiral trifluoroalkene. Ozonolysis followed by reduction of the resulting aldehyde results in 2(S),3(S),4(R) trifluorononanol, where X=Y=Z=F and R=n-butyl.

EXAMPLE 6

Preparation of
2-(4'-Octyloxyphenyl)-5-[(2R,3R)-2,3-difluorohexoxy]-2-pyrimidine This example illustrates the synthesis of dihaloalkoxy ethers by first coupling an epoxy tosylate with an aromatic core, then transforming the epoxy moiety into a dihalo moiety. The procedure is outlined in Scheme V.

6A: 4-n-Octyloxycyanobenzene

To a solution of cyanophenol (25 g) and potassium carbonate (58 g) in 2-butanone (320 ml) was added bromooctane (61 ml) at room temperature. The stirred mixture was heated under reflux for 48 hrs (i.e., until TLC revealed complete reaction). The mixture was filtered, after which the solvent and excess alkyl bromide were removed in vacuo to give a colorless liquid.

6B: 4-n-Octyloxybenzamidine hydrochloride

A solution of 6A (48 g) in anhydrous methanol (60 ml) and benzene (60 ml) was cooled to 0° C., and anhydrous hydrogen chloride was bubbled through until the solution was saturated (ca. 15 g). The reaction mixture was allowed to stir for 1 hr at 0° C. and was then placed in a 4° C. refrigerator for 48 hrs (i.e., until TLC revealed complete reaction). The solution was poured into ether (300 ml) and filtered. The white solid filtrant was washed with a further portion of ether (50 ml) and dried in a vacuum desiccator.

The filtrant was then dissolved in anhydrous ethanol (250 ml), and the resultant solution was cooled to 0° C. A chilled solution of ammonia in anhydrous ethanol (6M, 35 ml) was then added to the reaction mixture, and the mixture was stirred for 1 hr at 0° C. It was then allowed to stand at 4° C. for 48 hrs. The solution was then poured into ether (750 ml) and filtered. The white solid filtrant was washed with a further portion of ether (100 ml) and dried in a vacuum desiccator.

6C: 4'-Octyloxyphenyl-4-ethoxy-2-pyrimidine

To a solution of 6B (5 g) in pyridine (90 ml) was added 1-dimethylamino-3-dimethyliminio-2-ethoxypropene perchlorate (5.7 g), which was prepared according to Arnold (1973), Coll. Czech. Chem. Comm. 38: 1168. The solution was stirred at reflux for 16 hrs, at which time it was poured into a hydrochloric acid solution (1M, 200 ml) and extracted with three portions of ethyl acetate. The combined organic extracts were washed with brine and dried over sodium sulfate 16 hrs, at which time it was poured into a hydrochloric acid solution (1M, 30 ml) and extracted with three portions of ethyl acetate. The combined organic extracts were washed with brine and dried over sodium sulfate. The solvent was removed in vacuo to give a white powder.

6D: 2-(4'-Octyloxyphenyl)-5-hydroxypyrimidine

To a solution of 6C (5.5 g) in diethylene glycol (55 ml) was added sodium hydroxide (4.2 g). The solution was heated to 200° C. under nitrogen and stirred at this temperature for 8 hrs. The mixture was then poured into glacial acetic acid (70 ml), yielding a white precipitate. The precipitate was filtered, washed with 10 ml acetic acid and 15 ml water, then dried in a vacuum desiccator.

6E: 2-(4,-Octyloxyphenyl)-5-[(2R,3R)-2,3-epoxyhexoxy]-pyrimidine

To a mixture of 6D (521 mg), (S,S)-2,3-epoxyhexyl-1-tosylate (469 mg), and cesium carbonate (593 mg) in a dry flask was added dimethylformamide (5.2 ml). The solution was stirred for 48 hrs, then poured into a hydrochloric acid solution (1M, 15 ml) and extracted thrice with a 1:1 ethyl acetate:hexane mixture. The combined organic extracts were washed with brine and dried over sodium sulfate and potassium carbonate. The solvent was removed in vacuo to give a white solid.

6F: 2-(4'-Octyloxyphenyl)-5-[(2S,3R)-3-fluoro-2-hydroxyhexoxy]-pyrimidine

A mixture of 6E (598 mg) in dichloromethane (3 ml) in a polyethylene bottle was cooled to 0° C. and hydrogen fluoride-pyridine (0.43 ml) was added. The mixture was allowed to stir at 0° for 2 hours, then allowed to stand at 4° for 14 hours. At that time, it was poured into a saturated solution of sodium bicarbonate (10 ml) and extracted with three portions of dichloromethane. The combined organic extracts were dried over sodium sulfate and potassium carbonate, and the solvent and residual pyridine was removed in vacuo to yield a colorless oil. The compound was used without purification in the next reaction.

6G: 2-(4'-Octyloxyphenyl)-5-[(2R,3R)-2,3-difluorohexoxy]-2-pyrimidine

A mixture of 6F (628 mg) in dichloromethane (30 ml) was stirred and cooled to −70° C. Diethylaminosulfur trifluoride (DAST, 0.30 ml) was then added. The reaction mixture was allowed to warm to −20° C. over 1 hr, and at that time pyridine (0.24 ml) was added. The reaction was allowed to warm to room temperature over the course of several hours, and stirred for a total of 16 hrs. It was then poured into a pH 7 phosphate solution (30 ml) and extracted three times with dichloromethane. The combined organic extracts were dried over sodium sulfate and potassium carbonate, and the solvent was removed in vacuo to yield a white solid. The product was purified by flash chromatography using 1:4 ethyl acetate:hexanes and recrystallized successively from hexane and acetonitrile to give a compound with long white needles.

EXAMPLE 7

Preparation of
5-{4'-[(2R,3R)-2,3-difluorohexoxy]phenyl]}-2-octyl-pyrimidine

7A: 5-{4'-[(2R,3R)-2,3-Epoxyhexoxy]phenyl}-2octyl-pyrimidine

The method used was as for 6E. The starting phenol was prepared according to Zaschke et al., (1977) Z. Chem 17:293. See Scheme VI.
Quantities used:

| | |
|---|---|
| 5-(4'-hydroxyphenyl)-2-octylpyrimidine | 0.189 g |
| (S,S)-2,3-epoxyhexyl-1-tosylate | 0.180 g |
| Cs₂CO₃ | 0.227 g |
| DMF | 2 ml |

The compound was purified by flash chromatography using 1:4 ethyl acetate:hexane as the eluent, giving a white solid as the product.

7B: 5-{4'-[(2S,3R)-3-Fluoro-2-hydroxyhexoxy]Phenyl}-2-octylpyrimidine

The method used was as for 6F.
Quantities used:

| | |
|---|---|
| 7A | 47 mg |
| HF/pyridine | 35 μl |
| CH₂Cl₂ | 1 ml |

7C: 5-{4'-[(2R,3R)-2,3-Difluorohexoxy]phenyl}-2octylpyrimidine

The method used was as for 6G.
Quantities used:

| | |
|---|---|
| 7B | 74 mg |
| DAST | 50 μl |
| CH₂Cl₂ | 1 ml |
| pyridine | 75 μl |

The compound was purified by flash chromatography using 20% ethyl acetate in hexanes, giving a white solid.

EXAMPLE 8

Preparation of 5-{4'-[(2R,3R)-2,3-difluorohexoxy]phenyl]}-2-decylthiopyrimidine

8A: 5-{4'-[(2R,3R)-2,3-Epoxyhexoxy]phenyl}-2decylthiopyrimidine

The method used was as for 6E. The starting phenol was prepared according to Zaschke et al., (1977) Z. Chem 17:293. See Scheme VII.
Quantities used:

| | |
|---|---|
| 5-(4'-hydroxyphenyl)-2-decylthiopyrimidine | 0.600 g |
| (S,S)-2,3-epoxyhexyl-1-tosylate | 0.471 g |
| Cs₂CO₃ | 0.624 g |
| DMF | 5.2 ml |

The compound was used without purification in the next step.

8B: 5-{4'-[(2S,3R)-3-Fluoro-2-hydroxyhexoxy]phenyl}-2-decylthiopyrimidine

The method used was as for 6F.
Quantities used:

| | |
|---|---|
| 8A | 0.700 g |
| HF/pyridine | 0.45 ml |
| CH₂Cl₂ | 3 ml |

The product was used without purification in the next step.

8C: 5-{4'-[(2R,3R)-2,3-Difluorohexoxy]phenyl)-2-decylthiopyrimidine

The method used was as for 6G.
Quantities used:

| | |
|---|---|
| 8B | 0.731 g |
| DAST | 0.31 ml |
| CH₂Cl₂ | 16 ml |
| pyridine | 0.25 ml |

The product was purified by flash chromatography using 20% ethyl acetate in hexanes as the eluent, and was then recrystallized from acetonitrile to give white needles.

EXAMPLE 9

Preparation of 2-(4'-octyloxyphenyl)-5-{4'-[(2R,3R) difluorohexoxy]phenyl}-pyrimidine This example illustrates the synthesis of dihaloalkoxy ethers by the protection of an epoxy alcohol, transformation of the epoxy moiety into a dihalo moiety, deprotection of the alcohol, and subsequent coupling of the alcohol to an aromatic core. The procedure is outlined in Scheme VIII.

9A: 2-(4,-Octyloxyphenyl)-5-(4'-hydroxyphenyl)-pyrimidine

To a solution of 6B (1.16 g) in pyridine (6 ml) was added 1-dimethylamino-3-dimethyliminio-2-(4-hydroxyphenyl)-propene perchlorate (1 g) (Zaschke et al., supra) at room temperature. The solution was stirred at reflux for 16 hrs, at which time it was poured into a hydrochloric acid solution (1M, 30 ml) and extracted with three portions of ethyl acetate. The combined organic extracts were washed with brine and dried over sodium sulfate. The solvent was removed in vacuo to give a white powder, which was purified by flash chromatography using a 2:1 mixture of hexanes and ethyl acetate.

9B: (2S,3S)-Epoxyhexyl benzyl ether

To a solution of (2S,3S)-epoxyhexanol (10 g) in dichloromethane (54 ml) at room temperature was added benzyl chloride (12 ml) and tetrabutylammonium bromide (1.39 g). To the flask containing this solution was added an aqueous sodium hydroxide mixture (4.0 M, 65 ml). The reaction was allowed to stir rapidly for 48 hrs, at which time a further portion of tetrabutylammonium bromide (1.4 g) was added. The reaction was allowed to stir a further 24 hrs, at which time it appeared by TLC to be approximately 95% complete. The reaction mixture was partitioned and the aqueous layer was washed three times with dichloromethane. The combined dichloromethane fractions were then washed with a dilute sodium bicarbonate solution and dried over sodium sulfate and potassium carbonate. The solvent was removed by rotary evaporation, and the product distilled (1.8 torr, 122° C.) as a clear liquid.

9C: (2S,3R)-3-Fluoro-2-hydroxyhexyl benzyl ether

A solution of 9B (13.86 g) in dichloromethane (335 ml) was prepared in a polyethylene bottle and cooled with stirring to 0° C. To this solution was added hydrogen fluoride-pyridine (19.2 ml), and the reaction was stirred for 1.5 hrs (i.e., until TLC showed the reaction to be complete). The reaction was then slowly added to a flask containing a saturated sodium bicarbonate solution (300 ml). It is also possible to neutralize this reaction using phosphate buffer. The reaction was then partitioned and the aqueous layer extracted with dichloromethane. The combined organic fractions were dried over sodium sulfate and potassium carbonate, after which the solvent was removed in vacuo, yielding a clear oil, which was used in the next reaction without further purification.

9D: (2R,3R)-Difluorohexyl benzyl ether

To a solution of 9C (15.18 g) in dichloromethane (670 ml), cooled to −78° C., was added DAST (13.3 ml). The reaction was stirred, and allowed to warm to −35° C. over the course of two hours. At this time, pyridine (10.8 ml) was added to the mixture, which was then allowed to warm to room temperature over two hours, and stirred at room temperature for a further 14 hours. The reaction mixture was then slowly poured into a saturated sodium bicarbonate solution. The aqueous layer was extracted with three further portions of dichloromethane, and the combined organic extracts were dried over sodium sulfate and potassium carbonate. The product was purified by flash chromatography using 10% ethyl acetate in hexanes, and was further purified by Kugelrohr distillation (1 torr, ca 140° C.) to give a clear oil as the product.

9E: (2S,3S)-Difluorohexyl toluenesulfonate

To a solution of 9D (0,810 g) in anhydrous THF (20 ml) was added 10% palladium hydroxide on carbon (0.044 g). The reaction was stirred under an atmosphere of hydrogen for 200 hrs (i.e., until TLC showed the reaction to be complete). The reaction mixture was then cooled to 0° C., and to it was added toluenesulfonyl chloride (1.35 g) and pyridine (1.14 ml). The reaction was stirred 1 hour at 0°, then allowed to stand at 4° C. for 48 hrs (i.e., until TLC showed the reaction to be complete). To the solution was then added a small amount of water (ca. 200 μl) to hydrolyze any excess toluenesulfonyl chloride, and the solution was stirred at room temperature for two hours. The solution was then poured into water and extracted three times with ethyl acetate. The combined organic layers were washed with brine and dried over sodium sulfate and potassium carbonate. The solvent was removed in vacuo and the product was purified by flash chromatography using 10% ethyl acetate in hexanes as the eluent. The resulting compound was a solid which melted at approximately 28° C.

9F: 2-(4'-Octyloxyphenyl)-5-{4'-[(2R,3R) difluorohexoxy]phenyl}-pyrimidine

To a flask containing 9A (52 mg), 4D (40 mg), and cesium carbonate (46 mg) was added dimethylformamide (0.7 ml). The resulting solution was stirred 16 hrs at room temperature under a nitrogen atmosphere. The solution was then poured into water and extracted three times with a 1:1 mixture of hexanes and ethyl acetate. The combined organic phases were washed with brine and dried over sodium sulfate and potassium carbonate. The solvent was removed in vacuo and the product purified by flash chromatography using 15% ethyl acetate in hexanes as the eluent. The white solid product was recrystallized from acetonitrile.

EXAMPLE 10

Preparation of 5-{4'-[(2R,3R)-2,3-difluorohexoxy]phenyl}-2octyloxypyrimidine

See Scheme VIII.

10A: 5-{4'-[(2R,3R)-2,3-Difluorohexoxy]phenyl}-2octyloxypyrimidine

To a solution of 5-(4'-hydroxyphenyl)-2-octyloxypyrimidine (39 mg, prepared according to Zaschke et al., supra) and 4E (40 mg) in DMF (0.7 ml) was added cesium carbonate (47 mg). The solution was stirred for 48 hrs, at which time it was poured into water and extracted three times with a 1:1 mixture of hexanes and ethyl acetate. The combined organic phases were washed with brine and dried over sodium sulfate and potassium carbonate. The solvent was removed in vacuo and the product purified by flash chromatography using 15% ethyl acetate in hexanes as the eluent. The white solid product was recrystallized from acetonitrile.

EXAMPLE 11

The preparation of 2-{4'-[(2R,3R)-2,3-difluorohexoxy]phenyl}-5-octyloxypyridine

See Scheme IX.

11A: 2-Iodo-5-octyloxypyridine

To a solution of one gram of 2-iodo-5-hydroxypyridine (prepared as by Edgar, K. J. & Falling, S. N.; (1990) J. Org. Chem., 55: 5287) in dimethylformamide (14 ml) was added cesium carbonate (1.55 g) and bromooctane (1.56 ml). The reaction was allowed to stir for 100 hrs, at which time it was poured into water and extracted with 1:1 hexane:ethyl acetate. The combined organics were washed with brine and dried over sodium sulfate and potassium carbonate. The solvent was removed in vacuo to give a yellow oil. This oil was purified by flash chromatography using 10% ethyl acetate in hexanes as the eluent, giving a clear oil as a product.

11B: 4-Methoxy-phenylboronic acid

To a solution of 4-bromoanisole (2 g) in tetrahydrofuran (THF, 32 ml), which was cooled to −78° C., was added a hexane solution of n-butyllithium (0.83 M, 13.5 ml). The solution was stirred 15 minutes, at which time triisopropyl borate (8.6 ml) was added. The solution was stirred for 15 minutes, at which time the solution was allowed to warm to room temperature. Stirring was continued for 12 hrs. The solution was then washed into a hydrochloric acid solution (1M, 60 ml) with a small amount of THF. This solution was stirred an additional 2 hours, and was then extracted with ethyl acetate. The combined organic layers were washed with brine and dried over sodium sulfate, and the solvent was removed in vacuo to yield a white solid.

11C: 2-(4'-Methoxyphenyl)-5-octyloxypyridine

To a flask outfitted with a reflux condenser was added 6B (300 mg), 6A (600 mg), and palladium tetrakis(triphenylphosphine) (62 mg). To this mixture was added toluene (4 ml) and a sodium carbonate solution (2M, 4.5 ml). This solution was refluxed for 16 hrs, at which time it was acidified with hydrochloric acid and extracted with ethyl acetate. The combined organic layers were washed with brine and dried over sodium sulfate and potassium carbonate. The solvent was removed in vacuo. The product purified by flash chromatography using 20% ethyl acetate in hexanes as the eluent to give a yellow liquid.

11D: 2-(4'-Hydroxyphenyl)-5-octyloxypyridine

To a solution of 11C (100 mg) in dichloromethane, cooled to 0° C., was added a solution of boron tribromide in dichloromethane (1M, 0.76 ml). This solution was stirred at 0° C. for 4 hours, then allowed to stand at 4° C. an additional 16 hrs. The solution was then poured into a saturated sodium bicarbonate solution and extracted with dichloromethane. The combined organic layers were dried over sodium sulfate and the solvent removed in vacuo to give a white solid.

11E:
2-(4'-[(2R,3R)-2,3-Difluorohexoxy]phenyl}-5-octyloxypyridine

The method used was as for 9F
Quantities used:

| 9E | 16.6 mg |
|---|---|
| 11LD | 17 mg |
| Cs$_2$CO$_3$ | 19 mg |
| DMF | 0.3 ml |

This product was purified by flash chromatography using 15% ethyl acetate in hexanes as the eluent. The resulting white solid was then recrystallized from acetonitrile.

EXAMPLE 12

Preparation of
5-[(2R,3R)-2,3-difluorohexoxy]-2-(4'-octylphenyl)pyridine

See Scheme X.

12A: 4-Octylphenylboronic acid

The method used was as for 11B.
Quantities used:

| 4-octylphenylbromide | 5 g |
|---|---|
| THF | 37 ml |
| m2n-butyllithium | 2.58M, 7.3 ml |
| trimethylborate | 4.2 ml |
| hydrochloric acid | 1M, 37 ml |

The product was a white solid.

12B: 5-Hydroxy-2-(4'-octylphenyl)pyridine

The method used was as for 11C, except that dimethoxyethane was used for greater solubility, and a hydroxyiodopyridine was used as the halogenated aromatic species.
Quantities used:

| 12A | 583 mg |
|---|---|
| 2-iodo-5-hydroxypyridine | 500 mg |
| Pd(PPh$_3$)$_4$ | 78 mg |
| Dimethoxyethane | 4.5 ml |
| Na$_2$CO$_3$ | 5.6 ml |

The product was a white solid.

12C:
5-[(2R,3R)-2,3-Difluorohexoxy]-2-(4'-octylphenyl)pyridine

The method used was as for 9F.
Quantities used:

| 12B | 13 mg |
|---|---|
| 9E | 13.5 mg |
| Cs$_2$CO$_3$ | 16 mg |
| DMF | 0.5 ml |

The product was purified by flash chromatography using 15% ethyl acetate in hexanes as the eluent, and recrystallized from acetonitrile to give a white solid.

EXAMPLE 13

Preparation of
2-{4'-[(2S,3S)-2,3-difluorohexoxy]phenyl}-5-octylpyridine

See Scheme XI.

13A: 5-Bromo-2-(4'-methoxyphenyl)-pyridine

The method used is as for 11C.
Quantities:

| 11B | 641 mg |
|---|---|
| 2,5-dibromopyridine | 1 g |
| Pd(PPh$_3$)$_4$ | 146 mg |
| toluene | 8.4 ml |
| Na$_2$CO$_3$ | 10.5 ml |

13B: 5-Octyl-2-(4'-methoxyphenyl)-pyridine

To a flask containing 13A (1 g) and dichloro[1,3-bis(diphenylphosphino)propane]nickle(II) (15 mg, prepared as in Kumada et al., Org. Syn. Coll. Vol. VI, p 407) is added THF (11 ml) and octyl magnesium bromide (2M, 2.74 ml). The solution is refluxed for 16 hrs, then poured into water and extracted three times with ethyl acetate. The combined organic layers are washed with brine and dried over sodium sulfate, and the solvent is removed in vacuo.

13C: 5-Octyl-2-(4'-hydroxyphenyl)-pyridine

The method for this reaction is as for 11D.
Quantities:

| 13B | 1 g |
|---|---|
| CH$_2$Cl$_2$ | 16 ml |
| BBr$_3$ | 5.9 ml |

13D: 2-{4'-[(2R, 3R)
-2,3-difluorohexoxy]phenyl}-5-octylpyridine

The method used is as for 9F.
Quantities:

| | |
|---|---|
| 13C | 97 mg |
| 9E | 100 mg |
| Cs₂CO₃ | 117 mg |
| DMF | 1 ml |

Compound 13C has also been made by the following method:

13E: 4-Methoxyphenyl 2-chlorovinyl ketone

To a flask containing sodium methoxide (7 g) and toluene (200 ml) and stirred with an overhead mechanical stirrer was added, dropwise at room temperature, a solution of 4-methoxyacetophenone (15 g) and ethyl formate (9.5 g) in toluene (100 ml). This mixture was stirred at room temperature for 18 hrs. Water (200 ml) was then added with stirring, and the two layers were separated. The organic layer was washed a further time with water, and the aqueous layers were combined and washed with ether. The aqueous portion was then acidified with 6N HCl, and extracted with ethyl acetate. The organic layer was washed with brine and dried over sodium sulfate, and the solvent removed in vacuo to give a yellow oil which crystallized within ten minutes.

The product of this reaction was then dissolved in benzene (100 ml) and treated with thionyl chloride (15 ml) under refluxing conditions. The solvent was stripped and the product filtered though a pad of silica gel with 4:1 hexanes:ethyl acetate to give a yellow crystalline product, which was recrystallized from 2% ethyl acetate in hexanes.

13F: 1-Piperidyl-1-decene

To a flask containing piperidine (30 g) was added decyl aldehyde (55 g) and toluenesulfonic acid (30 mg), and the mixture was stirred for 2 hours. The mixture was then distilled under reduced pressure, with the first fraction being water and the second, clear fraction being the product.

13G: 4-Methoxyphenyl 3-octyl-4-piperidylbutadienyl ketone

To a dry flask containing a magnetic stir bar under an argon atmosphere was added 13E (8.68 g) and anhydrous ether (100 ml). To this mixture was added 13F (9.85 g) and dry triethylamine (4.76 g), and the mixture was allowed to stir for 18 hrs. The triethylamine was then removed in vacuo, and the mixture was poured onto a thick plug of silica gel and eluted with 10% ethyl acetate in hexanes to remove unreacted starting materials. The silica gel was then eluted with ethyl acetate to remove the product. The solvent was stripped to afford a dark orange oil, which was used in the next reaction without further purification.

13C: 5-Octyl-2-(4'-hydroxyphenyl)-pyridine

To a flask containing 13G (15.06 g) was added a solution of perchloric acid (35%, 30 ml). The resultant mixture was refluxed for one hour, then 100 ml water was added and the mixture was cooled to 0° C., at which time a precipitate was formed. The dark granular precipitate was filtered and washed with water. It was then dissolved in ether (100 ml), cooled to 0° C., and again filtered to give a yellow precipitate.

The yellow precipitate was placed in a flask, and ammonium acetate (3.7 g) and glacial acetic acid (60 ml) were added. The mixture was heated to reflux for one hour, then cooled and poured into water. The mixture was extracted with ether, and the combined organic layers were back-extracted twice with water and once with brine, then dried over sodium sulfate and stripped of solvent in vacuo.

The product of the previous reaction was then dissolved in a solution of concentrated hydrobromic acid (20 ml) and glacial acetic acid (60 ml), and the mixture was heated at reflux for 48 hrs. The cooled reaction mixture was poured into water and extracted with ethyl acetate, and the combined organic layers were washed twice with water, twice with a 10% sodium bicarbonate solution, and once with brine, then dried over sodium sulfate and stripped of solvent in vacuo. The product was purified by flash chromatography using 4:1 hexanes:ethyl acetate as the eluent.

EXAMPLE 14

Preparation of 5-[(2R,3R)-2,3-difluorohexoxy]-2-(4'-octyloxyphenyl)-pyridine

See Scheme XII.

14A: Octyloxyphenylboronic acid

The method used is as for 11B.
Quantities:

| | |
|---|---|
| Bromo-4-octyloxybenzene | 1 g |
| n-butyllithium | 2.58M, 1.39 ml |
| trimethylborate | 0.80 ml |
| THF | 7 ml |
| HCl | 1M, 7 ml |

14B: 5-Hydroxy-2-(4'-octyloxyphenyl)pyridine

The method used is as for 12B.
Quantities:

| | |
|---|---|
| 14A | |
| 2-iodo-5-hydroxypyridine | 500 mg |
| Pd(PPh₃)₄ | 53 ml |
| Dimethoxyethane | 4.2 ml |
| Na₂CO₃ | |

14C: 5-[(2R, 3R)-2,3-Difluorohexoxy]-2-(4'-octyloxyphenyl) pyridine

The method used is as for 9 F.
Quantities:

| | |
|---|---|
| 14B | 102 mg |
| 9E | 100 mg |
| Cs₂CO₃ | 117 mg |
| DMF | 1 ml |

EXAMPLE 15

Preparation of 2-[(2R,3R)-2,3-difluorohexoxy]-5-(4'-octyloxyphenyl)-pyridine

See Scheme XIII.

15A: 2-Hydroxy-5-(4'-octyloxyphenyl)pyridine

The method used is that for 12B.
Quantities:

| | |
|---|---|
| 14A | 543 mg |
| 5-iodo-2-hydroxypyridine | 500 mg |
| Pd(PPh3)4 | 73 mg |
| Dimethoxyethane | 4.2 ml |
| Na2CO3 | 5.3 ml |

15B:
2-[(2R,3R)-2,3-Difluorohexoxy]-5-(4'-octyloxyphenyl) pyridine

The method used is that of 9F.
Quantities:

| | |
|---|---|
| 15A | 102 mg |
| 9E | 100 mg |
| Cs2CO3 | 117 mg |
| DMF | 1 ml |

EXAMPLE 16

Preparation of
2-[(2R,3R)-2,3-difluorohexoxy]-5-(4'-octylphenyl)pyridine

See Scheme XIV.

16A 2-Hydroxy-5-(4'-octylphenyl)pyridine

The method used is that of 12B.
Quantities:

| | |
|---|---|
| 12A | 583 mg |
| 5-iodo-2-hydroxypyridine | 500 mg |
| Pd(PPh3)4 | 78 mg |
| Dimethoxyethane | 4.5 ml |
| Na2CO3 | 5.6 ml |

16B: 2-[(2R, 3R)-2,3-Difluorohexoxy]-5-(4'-octylphenyl) pyridine

The method used is that of 9F.
Quantities:

| | |
|---|---|
| 16B | 26 mg |
| 9E | 27 mg |
| Cs2CO3 | 32 mg |
| DMF | 0.5 ml |

The invention has been described and illustrated by reference to several preferred embodiments, but it is not intended to limit the invention by doing so. For example, in some cases, a single enantiomer of each chirally asymmetric compound has been prepared, it is intended that the invention encompass both enantiomers of each compound. It is also intended that the invention include mixtures of the two enantiomers of the same formula in which there is an excess of one enantiomer. It is further intended that the invention encompass not only the FLC dopant compounds of formulas I–VII, but also compositions or formulations in which these compounds are admixed with each other or with other compounds including LC and FLC materials.

We claim:

1. A chiral nonracemic compound having the formula:

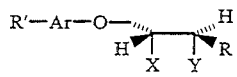

and enantiomers thereof, wherein:

Ar is a core unit containing at least two aromatic rings having the formula: $-A_a-(E)_e-B_b-(F)_f-D_d-$, where A, B and D, independently of one another, are selected from the group of aromatic rings consisting of phenyl, pyrimidine, pyridine, pyrazine, pyridizine, and thiadiazole, where a, b, and d, independently of one another, can be 0–3 and a+b+d=2 or 3, where E and F, independently of one another, are selected from the group —OOC—, —COO—, —CH2—$CH_2$—, —O—CH2—, —CH2—O—, —S—CH2—, and —CH2—S—, where e and f independently of one another are 0 or 1;

R' is an alkyl, alkenyl, alkoxy, thioalkyl, thioether, ether or silylalkyl group having three to fifteen carbon atoms;

X and Y are halogens; and

R is an alkyl or alkenyl group having from one to fifteen carbon atoms, provided that when R' is an alkyl group containing from three to fifteen carbon atoms, Ar is not 5,4'-substituted 2-phenylpyrimidine, 4,4'-substituted phenylbenzoate, 4,4,-substituted biphenylbenzoate or 4,4'-substituted biphenyl; and provided that when R' is an alkoxy group containing from three to fifteen carbon atoms, that Ar is not 4,4'-substituted phenylbenzoate, 4,4'-substituted biphenylbenzoate, or 4,4'-substituted biphenyl.

2. The chiral nonracemic compound of claim 1 wherein A, B and D, independently of one another, are selected from the group consisting of phenyl, pyridine, pyrimidine, pyridizine and pyrazine.

3. The chiral nonracemic compound of claim 1, wherein A, B and D are selected from the group phenyl, pyridine, pyrimidine, pyrazine, and pyridizine and wherein at least one of A, B or D is a nitrogen containing aromatic ring.

4. The chiral nonracemic compound of claim 1 wherein E and F are —OOC— or —COO— and e+f=1 and at least one of A, B or D is a nitrogen containing ring.

5. The chiral nonracemic compound of claim 1 wherein e and f are both 0 and at least one of A, B or D is a nitrogen containing ring.

6. The chiral nonracemic compound of claim 1 wherein Ar is selected from the group consisting of a 2-phenylpyridine, a 5-phenylpyridine, a 3-phenylpyridizine, 6phenylpyridizine, a 2-phenylpyrazine, a 3-phenylpyrazine, and a 5-phenylpyrimidine.

7. The chiral nonracemic compound of claim 1 wherein one or two of A, B or D are phenyl rings.

8. The chiral nonracemic compound of claim 1 wherein two of A, B, and D are phenyl rings and one of A, B, and D is a nitrogen containing aromatic.

9. The chiral nonracemic compound of claim 8 wherein e and f are both 0.

10. The chiral nonracemic compound of claim 1 wherein a, b, and d are all 1, A is a 2,5-disubstituted pyrimidine, B is a para-substituted phenyl, D is a para-substituted phenyl, e is 0, f is 1 and F is —COO—.

11. The chiral nonracemic compound of claim 1 wherein d, e and f are zero, a and b are 1 and A is a 2,5-disubstituted pyridine and B is a para-substituted phenyl.

12. The chiral nonracemic compound of claim 1 wherein d, e and f are zero, a and b are 1 and B is a 2,5-disubstituted pyridine and A is a para-substituted phenyl.

13. The chiral nonracemic compound of claim 1 wherein e and f are zero, a, b and d are 1 and A and D are phenyls and B is selected from the group consisting of 2,5-disubstituted pyridine, 2,5-disubstituted pyrimidine, 3,6-disubstituted pyridizine and 2,5-disubstituted pyrazine.

14. The chiral nonracemic compound of claim 1 wherein e and f are zero, a, b and d are 1 and A and D are phenyls and B is a 2,5-disubstituted pyrimidine.

15. The chiral nonracemic compound of claim 1 wherein E and F are selected from the group consisting of —CH₂—CH₂—, —O—CH₂—, —CH₂—O—, —S—CH₂—, and —CH₂—S—, and where e+f=1.

16. The chiral nonracemic compound of claim 15 wherein each of A, B and D is a phenyl ring.

17. The chiral nonracemic compound of claim 15 wherein Ar has two aromatic rings.

18. The chiral nonracemic compound of claim 15 wherein a+b+d is two and both rings of Ar are phenyl rings.

19. The chiral nonracemic compound of claim 1 wherein R' is an alkyl, alkenyl, alkoxy or thioalkyl group having from three to fifteen carbon atoms.

20. The chiral nonracemic compound of claim 1 wherein R' is an alkyl, e-alkenyl or alkoxy group having from three to fifteen carbon atoms.

21. The chiral nonracemic compound of claim 1 wherein R' is an alkyl group having from three to fifteen carbon atoms.

22. The chiral nonracemic compound of claim 1 wherein R' is a thioalkyl group having from three to fifteen carbon atoms.

23. The chiral nonracemic compound of claim 1 wherein R' is an e-alkenyl group having from three to fifteen carbon atoms.

24. The chiral nonracemic compounds of claim 1 wherein X, and Y are fluorines or chlorines.

25. The chiral nonracemic compounds of claim 1 wherein X, and Y are fluorines.

26. The chiral nonracemic compound of claim 1 wherein R is an alkyl group having from two to eight carbon atoms.

27. The chiral nonracemic compound of claim 1 wherein Ar is a 2,5-diphenylthiadiazole ring.

28. The chiral nonracemic compound of claim 11 wherein one of E or F is —COO—.

29. The chiral nonracemic compound of claim 11 wherein Ar is a core unit selected from the group consisting of:

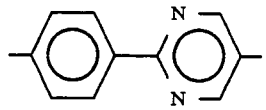

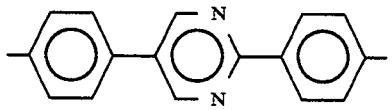

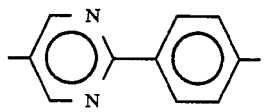

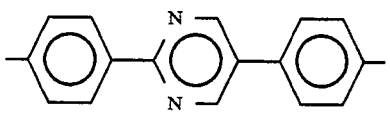

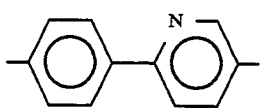

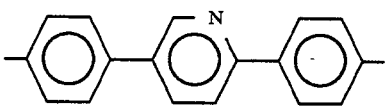

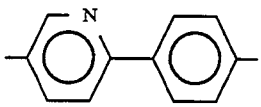

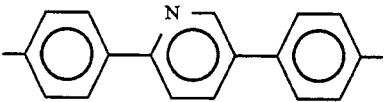

and wherein R' is an alkoxy group having three to fifteen carbon atoms; X and Y are fluorines; and R is an alkyl or alkenyl group having from one to fifteen carbon atoms.

* * * * *